(12) United States Patent
Saroka et al.

(10) Patent No.: US 12,207,900 B2
(45) Date of Patent: *Jan. 28, 2025

(54) METHOD OF PRODUCING AN ELECTROMAGNETIC (EM) PROBE

(71) Applicant: Sensible Medical Innovations Ltd., Netanya (IL)

(72) Inventors: Amir Saroka, Herzlia (IL); Benyamin Almog, Kibbutz Givat Brenner, IL (US); Shlomi Bergida, Ein Sarid (IL)

(73) Assignee: Sensible Medical Innovations Ltd., Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/217,637

(22) Filed: Jul. 3, 2023

(65) Prior Publication Data

US 2023/0337920 A1    Oct. 26, 2023

Related U.S. Application Data

(60) Continuation of application No. 17/693,460, filed on Mar. 14, 2022, now Pat. No. 11,690,515, which is a
(Continued)

(51) Int. Cl.
*A61B 5/00* (2006.01)
*A61B 5/0507* (2021.01)

(52) U.S. Cl.
CPC .......... *A61B 5/0064* (2013.01); *A61B 5/0082* (2013.01); *A61B 5/0507* (2013.01); *Y10T 29/49016* (2015.01); *Y10T 29/49204* (2015.01)

(58) Field of Classification Search
CPC ........ B65D 2581/3494; B65D 81/3453; A61B 5/0507; A61B 5/05; A61B 5/0064; H01Q 17/00; Y10T 29/49016; Y10T 29/49
(Continued)

(56) References Cited

U.S. PATENT DOCUMENTS

| | | |
|---|---|---|
| 2,414,376 A | 1/1947 | Heim |
| 4,344,440 A | 8/1982 | Aaby et al. |

(Continued)

FOREIGN PATENT DOCUMENTS

| | | |
|---|---|---|
| CN | 1870934 | 11/2006 |
| CN | 101198371 | 6/2008 |

(Continued)

OTHER PUBLICATIONS

Advisory Action Before the Filing of an Appeal Brief Dated Feb. 1, 2017 Re. U.S. Appl. No. 13/882,745. (3 pages).
(Continued)

*Primary Examiner* — Thiem D Phan

(57) ABSTRACT

An electromagnetic (EM) probe for monitoring one or more biological tissues. The EM probe comprises a cup shaped cavity having an opening and an interior volume, a circumferential flange formed substantially around the cup shaped cavity, in proximity to the opening, at least one layer of a material, for absorbing electromagnetic radiation, applied over at least one of a portion of the circumferential flange and a portion of the outer surface of the cup shaped cavity, and at least one EM radiation element which performs at least one of emitting and capturing EM radiation via the interior volume.

20 Claims, 19 Drawing Sheets

Related U.S. Application Data continuation of application No. 16/734,530, filed on Jan. 6, 2020, now Pat. No. 11,278,204, which is a continuation of application No. 15/619,723, filed on Jun. 12, 2017, now Pat. No. 10,524,662, which is a division of application No. 13/882,745, filed as application No. PCT/IL2011/050003 on Nov. 3, 2011, now Pat. No. 9,675,251.

(60) Provisional application No. 61/409,565, filed on Nov. 3, 2010.

(58) Field of Classification Search
USPC .................. 29/600, 428, 592.1, 601, 787
See application file for complete search history.

(56) References Cited

U.S. PATENT DOCUMENTS

| | | | |
|---|---|---|---|
| 4,755,828 | A | 7/1988 | Grim |
| 4,758,841 | A | 7/1988 | Grim |
| 6,454,711 | B1 | 9/2002 | Haddad et al. |
| 6,849,046 | B1 | 2/2005 | Eyal-Bickels et al. |
| 6,977,498 | B2 * | 12/2005 | Scherzinger ........... G01B 7/105 |
| | | | 324/229 |
| 7,591,792 | B2 | 9/2009 | Bouton |
| 7,825,667 | B2 | 11/2010 | Fang |
| 8,147,423 | B2 | 4/2012 | Hashimshony |
| 8,235,949 | B2 | 8/2012 | Hack et al. |
| 8,721,565 | B2 * | 5/2014 | Hashimshony ...... A61B 5/6834 |
| | | | 600/587 |
| 10,524,662 | B2 | 1/2020 | Saroka |
| 2003/0187366 | A1 | 10/2003 | Hashimshony |
| 2005/0119648 | A1 | 6/2005 | Swanson |
| 2007/0123770 | A1 | 5/2007 | Bouton et al. |
| 2007/0208404 | A1 | 9/2007 | Jones et al. |
| 2008/0198083 | A1 | 8/2008 | Yamaguchi |
| 2013/0225989 | A1 | 8/2013 | Saroka et al. |
| 2017/0273562 | A1 | 9/2017 | Saroka et al. |
| 2020/0138294 | A1 | 5/2020 | Saroka et al. |
| 2022/0192499 | A1 | 6/2022 | Saroka et al. |

FOREIGN PATENT DOCUMENTS

| | | |
|---|---|---|
| WO | WO 99/39728 | 8/1999 |
| WO | WO 00/64343 | 11/2000 |
| WO | WO 2006/085052 | 8/2006 |
| WO | WO 2006/133065 | 12/2006 |
| WO | WO 2009/031149 | 3/2009 |
| WO | WO 2011/141915 | 11/2011 |
| WO | WO 2012/059929 | 5/2012 |

OTHER PUBLICATIONS

Advisory Action Before the Filing of an Appeal Brief Dated Jan. 23, 2017 Re. U.S. Appl. No. 13/882,745. (3 pages).

Advisory Action Before the Filing of an Appeal Brief Dated May 24, 2016 Re. U.S. Appl. No. 13/882,745.

Communication Pursuant to Article 94(3) EPC Dated Aug. 2, 2017 From the European Patent Office Re. Application No. 11796831.3. (4 Pages).

Communication Pursuant to Article 94(3) EPC Dated Mar. 6, 2019 From the European Patent Office Rc. Application No. 11796831.3. (7 Pages).

Communication Pursuant to Article 94(3) EPC Dated May 11, 2020 From the European Patent Office Re. Application No. 11796831.3. (6 Pages).

International Preliminary Report on Patentability Dated May 16, 2013 From the International Bureau of WIPO Re. Application No. PCT/IL2011/050003.

International Search Report and the Written Opinion Dated Feb. 21, 2012 From the International Searching Authority Re. Application No. PCT/IL2011/050003.

Notice of Allowance Dated Feb. 7, 2023 Re. U.S. Appl. No. 17/693,460. (5 pages).

Notice of Allowance Dated Feb. 10, 2017 Re. U.S. Appl. No. 13/882,745. (3 pages).

Notice of Allowance Dated Nov. 15, 2021 together with Interview Summary Re. U.S. Appl. No. 16/734,530. (7 pages).

Notice Of Allowance Dated Aug. 28, 2019 Re. U.S. Appl. No. 15/619,723. (7pages).

Notification of Office Action Dated Jan. 12, 2015 From the State Intellectual Property Office of the People's Republic of China Re. Application No. 201180064044.5.

Notification of Office Action Dated Jul. 28, 2014 From the State Intellectual Property Office of the People's Republic of China Re. Application No. 201180064044.5 and Its Translation Into English.

Official Action Dated Oct. 3, 2022 Re. U.S. Appl. No. 17/693,460. (10 pages).

Official Action Dated Oct. 8, 2015 Re. U.S. Appl. No. 13/882,745.

Official Action Dated Aug. 10, 2016 Re. U.S. Appl. No. 13/882,745.

Official Action Dated Feb. 12, 2016 Re. U.S. Appl. No. 13/882,745.

Official Action Dated Apr. 27, 2021 Re. U.S. Appl. No. 16/734,530. (9 pages).

Official Action Dated Nov. 28, 2018 Re. U.S. Appl. No. 15/619,723. (10 pages).

Restriction Official Action Dated Jun. 11, 2015 Re. U.S. Appl. No. 13/882,745.

Search Report Dated Jul. 28, 2014 From the State Intellectual Property Office of the People's Republic of China Re. Application No. 201180064044.5 and Its Translation Into English.

Translation Dated Jan. 25, 2015 of Notification of Office Action Dated Jan. 12, 2015 From the State Intellectual Property Office of the People's Republic of China Re. Application No. 201180064044. 5.

* cited by examiner

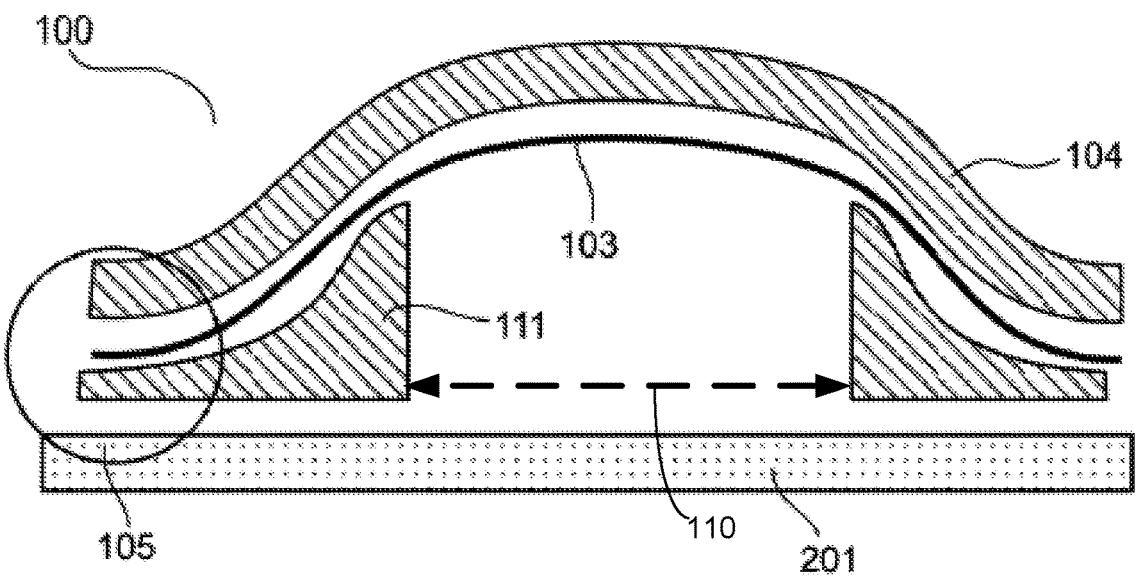
FIG. 6
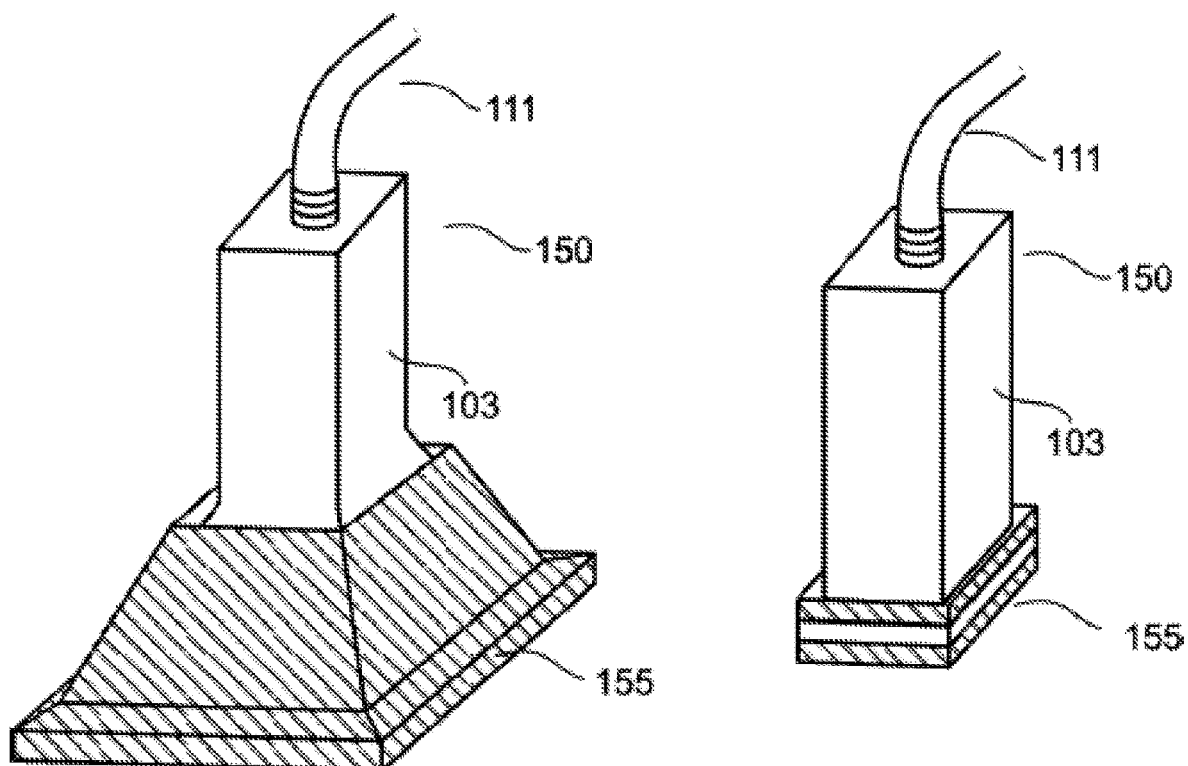
FIG. 7A
FIG. 7B

METHOD OF PRODUCING AN ELECTROMAGNETIC (EM) PROBE

RELATED APPLICATIONS

This application is a continuation of U.S. patent application Ser. No. 17/693,460 filed on Mar. 14, 2022, now U.S. Pat. No. 11,690,515, which is a continuation of U.S. patent application Ser. No. 16/734,530 filed on Jan. 6, 2020, now U.S. Pat. No. 11,278,204, which is a continuation of U.S. patent application Ser. No. 15/619,723 filed on Jun. 12, 2017, now U.S. Pat. No. 10,524,662, which is a division of U.S. patent application Ser. No. 13/882,745 filed on May 1, 2013, now U.S. Pat. No. 9,675,251, which is a National Phase of PCT Patent Application No. PCT/IL2011/050003 having International Filing Date of Nov. 3, 2011, which claims the benefit of priority of U.S. Provisional Patent Application No. 61/409,565 filed on Nov. 3, 2010. The contents of the above applications are all incorporated by reference as if fully set forth herein in their entirety.

FIELD AND BACKGROUND OF THE INVENTION

The present invention, in some embodiments thereof, relates to an electromagnetic EM probe and, more particularly, but not exclusively, to an EM probe for transmission and/or reception of electromagnetic radiation and a method of generating the EM probe.

EM radiation, such as RF and MW radiation, is potentially useful means of monitoring and diagnosing body tissues. The dielectric properties of the tissues may be a basis of detecting various pathologies and physiological trends. Examples for using RF and MW radiation for monitoring and diagnosing body tissues is found, inter alia, in International patent application pub. No WO 2010/100649, International patent application pub. No WO 2009/031150, and/or International patent application pub. No 2009/031149, which are incorporated herein by reference. The design and fabrication of such EM probes present various challenges.

During the last years, various EM probes have been developed. For example U.S. Pat. No. 6,233,479 describes a Microwave Hematoma Detector which is a non-invasive device designed to detect and localize blood pooling and clots near the outer surface of the body. While being geared towards finding subdural and epidural hematomas, the device can be used to detect blood pooling anywhere near the surface of the body. Modified versions of the device can also detect pneumothorax, organ hemorrhage, atherosclerotic plaque in the carotid arteries, evaluate perfusion (blood flow) at or near the body surface, body tissue damage at or near the surface (especially for burn assessment) and be used in a number of NDE applications. The device is based on low power pulsed microwave technology combined with a specialized antenna, signal processing/recognition algorithms and a disposable cap worn by the patient which will facilitate accurate mapping of the brain and proper function of the instrument. The invention may be used for rapid, non-invasive detection of subdural or epidural hematoma in human or animal patients, detection of hemorrhage within approximately 5 cm of the outer surface anywhere on a patient's body.

Another example is described in U.S. Pat. No. 7,184,824 which describes an EM probe for examining tissue in order to differentiate it from other tissue according to the dielectric properties of the examined tissue are provided. The EM probe includes an inner conductor, having a plurality of sharp, thin, conductive spikes, at a proximal end with respect to a tissue for examination, the plurality of sharp, thin, conductive spikes being operative to enhance the electrical fringe fields, where interaction with the tissue for examination occurs.

Another example is described in U.S. Pat. No. 7,591,792 which describes: a tissue sensors house for one or more sensor elements. Each element has a housing mounted substrate and a superstrate with a planar antenna between. A transitional periphery (TP) of a superstrate outer surface interconnects a base to a plateau. At least some of the TP has a generally smooth transition. Plural elements are spaced by the housing. Alternately, the superstrate TP is flat, the housing extends to the outer superstrate surface and a shield surrounds the element. The housing is flush with or recessed below the superstrate and defines a TP between the housing and superstrate. A method converts a reference signal to complex form; plots it in a complex plane as a reference point (RP); converts a measurement signal to complex form; plots it in the complex plane as a measurement point (MP); determine a complex distance between the MP and the RP; and compares complex distance to a threshold.

SUMMARY OF THE INVENTION

According to some embodiments of the present invention there is provided an electromagnetic (EM) probe for monitoring at least one biological tissue. The EM probe comprises a cup shaped cavity having an opening and an interior volume, a circumferential flange formed substantially around the cup shaped cavity, in proximity to the opening, at least one layer of a material, for absorbing electromagnetic radiation, applied over at least one of a portion of the circumferential flange and a portion of the outer surface of the cup shaped cavity, and at least one EM radiation element which performs at least one of emitting and capturing EM radiation via the interior volume.

Optionally, the at least one layer covers at least the edge of the bottom surface of the circumferential flange.

Optionally, the portion of the at least one layer covers at least 25% of the bottom surface of the circumferential flange.

Optionally, at least part of the circumferential flange is set to be detachably connected to the cup shaped cavity.

More optionally, the circumferential flange is set to be affixed to a monitored user so as to allow detachably connecting the cup shaped cavity thereto, in a manner that the opening faces a skin area of the monitored user.

Optionally, the at least one EM radiation element is placed in the interior volume.

Optionally, the at least one EM radiation element is placed outside of the interior volume and connected by a waveguide to the cup shaped cavity.

Optionally, the circumferential flange and cup shaped cavity are molded as a single unit.

Optionally, the at least one layer is applied over at least one of a bottom side of the circumferential flange and a top side of the circumferential flange.

Optionally, the circumferential flange is non continuous.

Optionally, the circumferential flange is at least partly flexible.

Optionally, the circumferential flange is at least partly rigid.

Optionally, the circumferential flange is zigzagged along a plane parallel to the opening.

Optionally, the EM probe further comprises a processing unit, electrically connected to the emitting element, which performs at least one of controlling a transmission parameter of the emitted EM radiation and monitoring a biological tissue according to the captured EM radiation.

Optionally, the distance between the peripheral outer edge and the peripheral inner edge of the circumferential flange is at least 0.3 centimeters.

Optionally, the cup shaped cavity having a structure shape selected from a group consisting of: a box, a cube, a dome, a cone, and a pyramid.

Optionally, the EM radiation is reflected from a biological medium being in touch with the edges of the opening.

Optionally, the EM radiation is emitted by another EM radiation source, via a biological medium being substantially in front of the opening.

Optionally, the EM radiation source is another EM probe as defined in claim 1.

Optionally, the interior volume is filled with a dielectric substance.

Optionally, the EM probe is fabricated by a printed circuit board (PCB) fabrication method.

Optionally, the EM radiation is selected from a group consisting of radiofrequency (RF) radiation and microwave (MW) radiation.

Optionally, the circumferential flange is a non circular circumferential flange.

Optionally, the circumferential flange is at least partly inside the cup shaped cavity.

Optionally, the circumferential flange is configured to form an airtight interface with a skin area of a patient, the airtight interface set to attach the EM probe to a skin area of a patient by air pressure differences.

Optionally, the EM probe is an intrabody probe.

According to some embodiments of the present invention there is provided a method of producing an electromagnetic (EM) probe for monitoring at least one biological tissue. The method comprises providing a cup shaped cavity having an opening and an interior volume, forming a circumferential flange substantially around the cup shaped cavity, applying at least one layer of a material for absorbing electromagnetic radiation over at least one of a portion of the circumferential flange and a portion of the outer surface of the cup shaped cavity, placing an emitting element configured for at least one of emitting and capturing EM radiation, and electrically connecting the emitting element to at least one of an EM receiver and an EM transmitter.

According to some embodiments of the present invention there is provided a method of monitoring at least one biological tissue. The method comprises providing a probe having a cup shaped cavity having an opening and an interior volume, a circumferential flange formed substantially around the cup shaped cavity, in proximity to the opening, at least one layer of a material, for absorbing electromagnetic radiation, applied over at least one of a portion of the circumferential flange and a portion of the outer surface of the cup shaped cavity, and at least one EM radiation element which performs at least one of emitting and capturing EM radiation via the interior volume and attaching the probe to a monitored user in a manner that the opening faces a skin area of the monitored user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 is a schematic sectional illustration of an EM probe for monitoring at least one biological tissue having a dome shaped cavity, according to some embodiments of the present invention;

FIGS. 7A and 7B are schematic illustrations of an EM probe having an EM element placed outside of the interior volume of a cup shaped cavity, according to some embodiments of the present invention;

DESCRIPTION OF SPECIFIC EMBODIMENTS OF THE INVENTION

Figure 1:
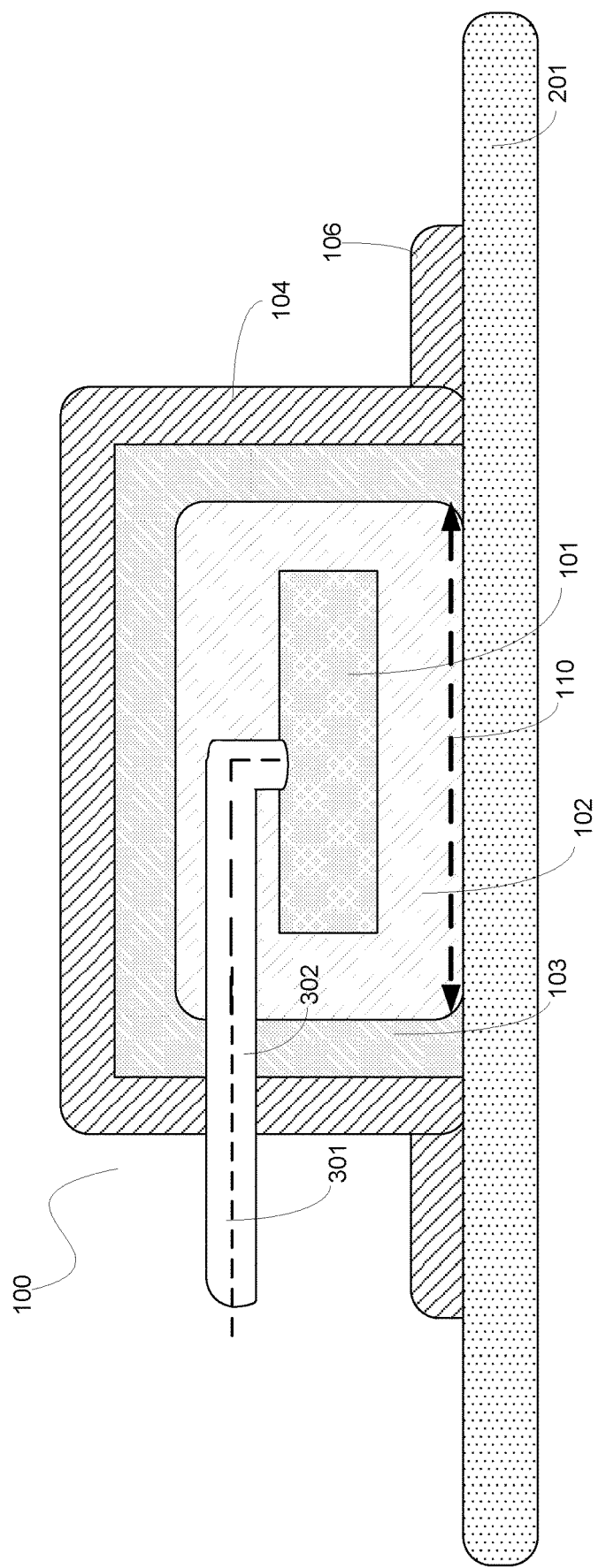
FIG. 1 is a schematic sectional illustration of an electromagnetic (EM) radiation EM probe for monitoring at least one biological tissue, according to some embodiments of the present invention.

The present invention, in some embodiments thereof, relates to an electromagnetic EM probe and, more particularly, but not exclusively, to an EM probe for transmission and/or reception of electromagnetic radiation and a method of generating the EM probe.

According to some embodiments of the present invention, there is provided an electromagnetic (EM) probe for monitoring dielectric properties in one or more biological tissues using a cup shaped cavity which is coated with one or more layers of absorbent material and has a circumferential flange. The cup shaped cavity houses an element for radiating and/or capturing EM radiation and has a single opening for the passage of the EM radiation. In such a manner, the cup shaped cavity forms a closed interference reduced volume when the opening is placed on top of or above a skin area of a monitored user. Such an EM probe is less sensitive to changes in the skin in an area outside the circumference of the EM probe, for example more than 2 cm, or more than 4 cm, and/or to changes which are introduced when the EM probe is being touched and/or changes which are related to the mechanical interfacing and/or coupling of the EM probe to the skin.

The circumferential flange is set to reduce the sensitivity to noise from the proximity of the EM probe, for example from external EM transmission sources, such as, for example, cellular phones, thus improving the signal to noise ratio (SNR) and therefore on the quality of reception. Moreover, the circumferential flange and the absorbing layers prevent from at least some of the EM transmissions to make their way to the external surface of the EM probe. In such a manner, the amount of escaped signals which add noise to the external environment may be reduced. It may reduce currents escaping or penetrating the EM probe to/from the external side of the EM probe or exposed body surfaces. Such currents may be conducted on the skin, or external conductive parts of the EM probe, like its cavity and/or conducting elements, such as cables. Such currents may, for example, be induced by currents related to a transmitting EM probe, or its connected cables, onto the conductive parts, or proximate skin area, of a receiving EM probe, via conduction or induction, resulting in parasitic crosstalk between them. The circumferential flange may be placed on the edge of the opening or attached to the external walls of the cup shape cavity few millimeters above the opening.

The circumferential flange may be a bendable flange and/or a flexible flange which is adjusted to be closely attached to the skin surface of a monitored user. Optionally the flange is also set to assist in prevention of entry of fluid and/or water and/or perspiration into the area under the EM probe. Optionally, the flange is set to enable an airtight interface of the EM probe to the skin area, enabling attachment by air pressure differences of the EM probe, and/or increasing the effectiveness of the isolation functionality of the flange by improving the mechanical coupling of the flange to the skin area. For example by use of another layer, for example a sub millimeter layer of silicon material, covering the bottom side of the flange. The circumferential flange may be zigzagged, jagged, and/or curved to extend the path of signals passing therethrough.

The absorbing material may cover external walls of the cup shaped cavity, the circumferential flange or any portion thereof, and/or a portion of the internal walls of the cup shaped cavity. A layer of absorbing material may be placed on the lower side of the circumferential flange so as to be in contact with the monitored skin area.

According to some embodiments of the present invention, the EM probe is a printed circuit board (PCB) EM probe fabricated in known fabrication techniques.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic sectional illustration of an electromagnetic (EM) radiation EM probe 100 for monitoring at least one biological tissue, according to some embodiments of the present invention. The EM probe 100 includes a cup shaped cavity 103 having an opening 110 and an interior volume 102. As FIG. 1 depicts a section illustration, the depicted broken line represents the diameter of the opening 110. The outer surface of the cup shaped cavity 103, namely the external sides of the cup shaped cavity 103 which do not face the interior volume 102 are covered with one or more layers 104 of a material for absorbing EM radiation. The one or more layers 104 are set to absorb electric fields and/or magnetic fields.

For example regarding the complex permittivity of the absorbing material at a frequency of about 1 Ghz, $\varepsilon'$ is between 2 and 60 typically around 30 and $\varepsilon''$ is between 1 and 30 typically 5 and regarding the complex permeability of the absorbing material, $\mu'$ is between 1 and 30 typically 20 and $\mu''$ is between 2 and 30 typically 6 to 15. The cup shaped cavity 103, which may be referred to as a cavity is made of a conductive material. The absorbing material may be any material that dissipates EM energy, for example Eccosorb® MCS, GDS and BSR, which the specifications thereof are incorporated herein by reference. Optionally, the thickness of the one or more layers 104 is between about 0.1 millimeters (mm) and about 10 cm.

Optionally, the height of the cup shaped cavity 103 is between about 0.5 millimeters (mm) and about 10 cm. Optionally, the width of the opening 110 of the cup shaped cavity 103 is between about 0.5 millimeters (mm) and about 20 centimeters.

Optionally, the opening width is set according to the transmitted and/or received frequency and/or the size or configuration of the EM element(s).

Optionally, the cup shaped cavity 103 comprises a plurality of chambers wherein in each chamber contains a different EM element, such as the EM element 101. The plurality of EM elements can also be used inside a single non-divided or partly chambered cavity.

The one or more layers 104 are applied, for example laminated, on the cup shaped cavity 103 and/or molded as cup sized and shaped to engulf the cup shaped cavity 103 without blocking the opening 110. The cup shaped cavity 103 is optionally shaped to have a cubical outline, a cylindrical outline, a dome outline, a pyramid outline, or a conical outline, each having an open base set for being in direct or indirect (for example, via intermediate substance) contact with a skin tissue of a monitored, diagnosed EM probed, and/or monitored user. Optionally, the cup shaped cavity 103 is made of a conductive material, such as metal. Optionally and respectively the one or more layers 104 has a respective outline.

Optionally, the one or more layers 104 are extended to increase the surface area of absorbing material which is found above the space between the skin area above a monitored intrabody target area and the EM probe 100.

Figure 2:
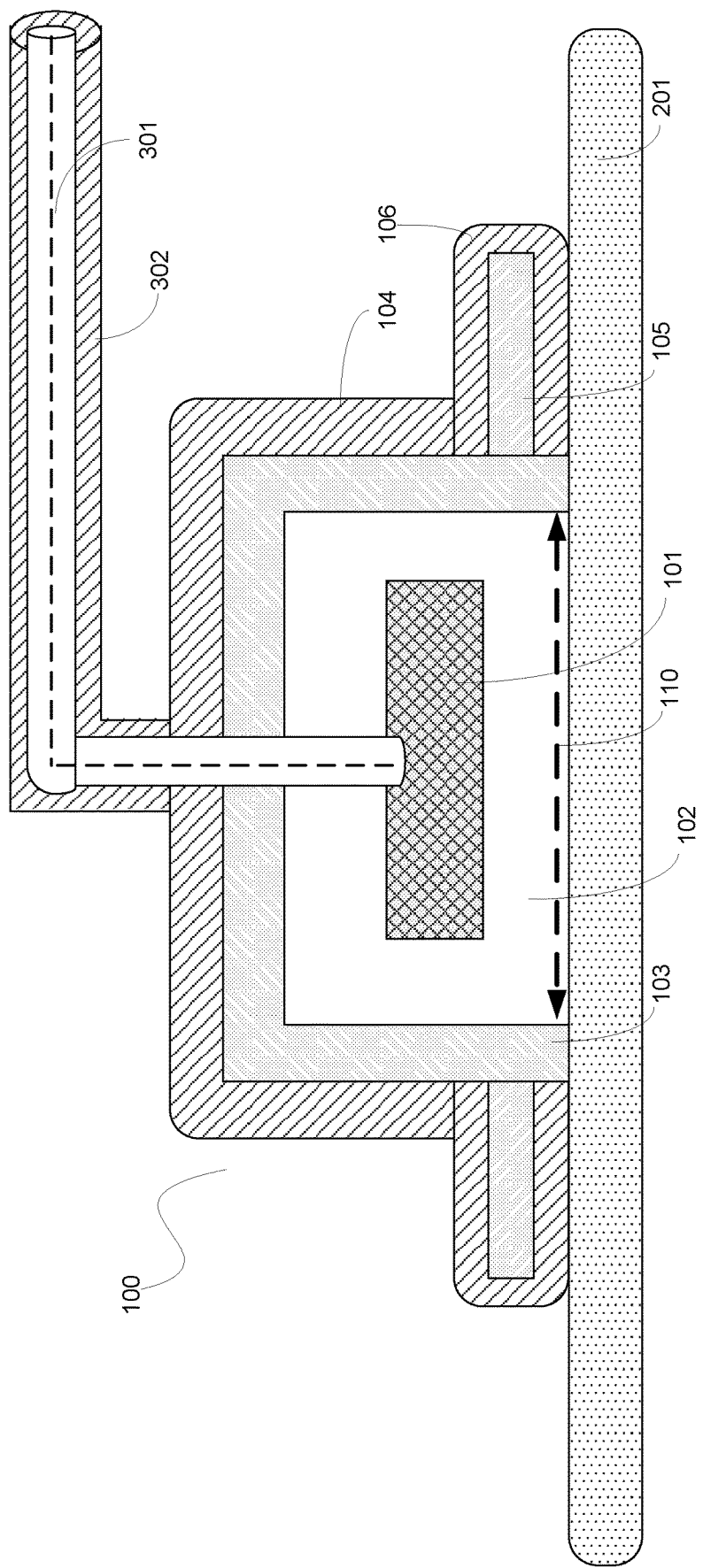
FIG. 2 is a schematic sectional illustration of an EM probe for monitoring at least one biological tissue having a circumferential flange, according to some embodiments of the present invention.

The EM probe 100 further includes one or more emitting and/or receiving elements 101 which are placed in the interior volume 102. Optionally, the EM radiation is radio frequency (RF) radiation and/or microwave (MW) radiation for example from a few 100 MHz's up to a few GHz. The emitting and/or receiving elements 101 are connected, by conducting element(s) 301, such as cables, for example coaxial cables, and/or waveguides, for example metal tubes used to carry microwave and/or RF energy with little loss of power, to external means for generating and/or analyzing EM signals, as further described below. The conducting element(s) 301 may be connected to the emitting and/or receiving elements 101 via an aperture in the lateral walls of the cup shaped cavity 103 and/or an aperture in the top wall of the cup shaped cavity 103, for example as shown in FIG. 2. As used herein, an emitting and/or receiving element means a transducer, an antenna, for example a bowtie antenna, an ultra-wide band (UWB) antenna, a micro strip antenna, a slot fed antenna, a dipole antenna, a patch antenna, and a spiral element antenna, a feedhorn and/or a tip of a waveguide which delivers and/or collects EM radiation. For example, in FIG. 1, an antenna is connected via a coaxial cable 301 to an external means for generating and/or analyzing EM signals (not shown).

Optionally, the interior volume 102 remains empty and therefore filled with air when being used. Optionally, the interior volume 102 is filled with a dielectric substance having a relatively high dielectric coefficient, for example about 10, such as Rogers R3010. Optionally, the dielectric substance has a dielectric coefficient which relatively matches the dielectric coefficient of body tissues or any matching material in-between. In such a manner, dielectric discontinuity is reduced and the efficiency of the transmission of the emitting element 101 and the sensitivity of the EM receiving element 101 is increased. Optionally, a layer of dielectric material, elastic, shape preserving or other, or a composition of different materials, such as a gel with or without dielectric increasing agents, for example metal oxides or fluids, and is applied between the EM probe and the skin area 201. Optionally separating the layer of dielectric material and the skin is a layer of a biocompatible material.

Reference is now made to FIG. 2, which is a schematic sectional illustration of an EM probe 100 for monitoring at least one biological tissue, according to some embodiments of the present invention. The EM probe 100 is similar to the one depicted in FIG. 1, however it further includes a circumferential flange 105 that is attached to the cup shaped cavity 103, in proximity to the opening 110, for example few millimeters above the opening edge, as shown in FIG. 2 or on the same plane of the opening edge, as depicted in FIG. 3.

The circumferential flange 105 is placed around the opening 110, optionally so as to be parallel to a skin area 201 in proximity to a monitored, EM probed, and/or diagnosed tissue(s) of a monitored user in proximity to the skin area 201 about implanted antenna. The circumferential flange 105 is made of a conductive material, such as metal. The circumferential flange 105, which is optionally a non-circular or circular metal ring, surrounds the opening and is electrically coupled, for example galvanically connected, to the cup shaped cavity 103. Optionally, the circumferential flange 105 is an integral part of the cup shaped cavity 103. For example the circumferential flange 105 is a portion of the cup shaped cavity 103 that is bended to be substantially in parallel or in parallel to the skin area of a monitored, EM probed, and/or diagnosed tissue(s) of a monitored user.

It should be noted that the EM probe 100 may be part of an intrabody implant, such as a subdermal implant. In such an embodiment, the EM probe 100 is sized and shaped to be placed between the tissues. In such an embodiment, the opening 110 may directly face a fat layer or a muscle layer. In such embodiments, the aforementioned structure of the EM probe 100 reduces currents that may develop on the tissue surface.

Figure 3A:
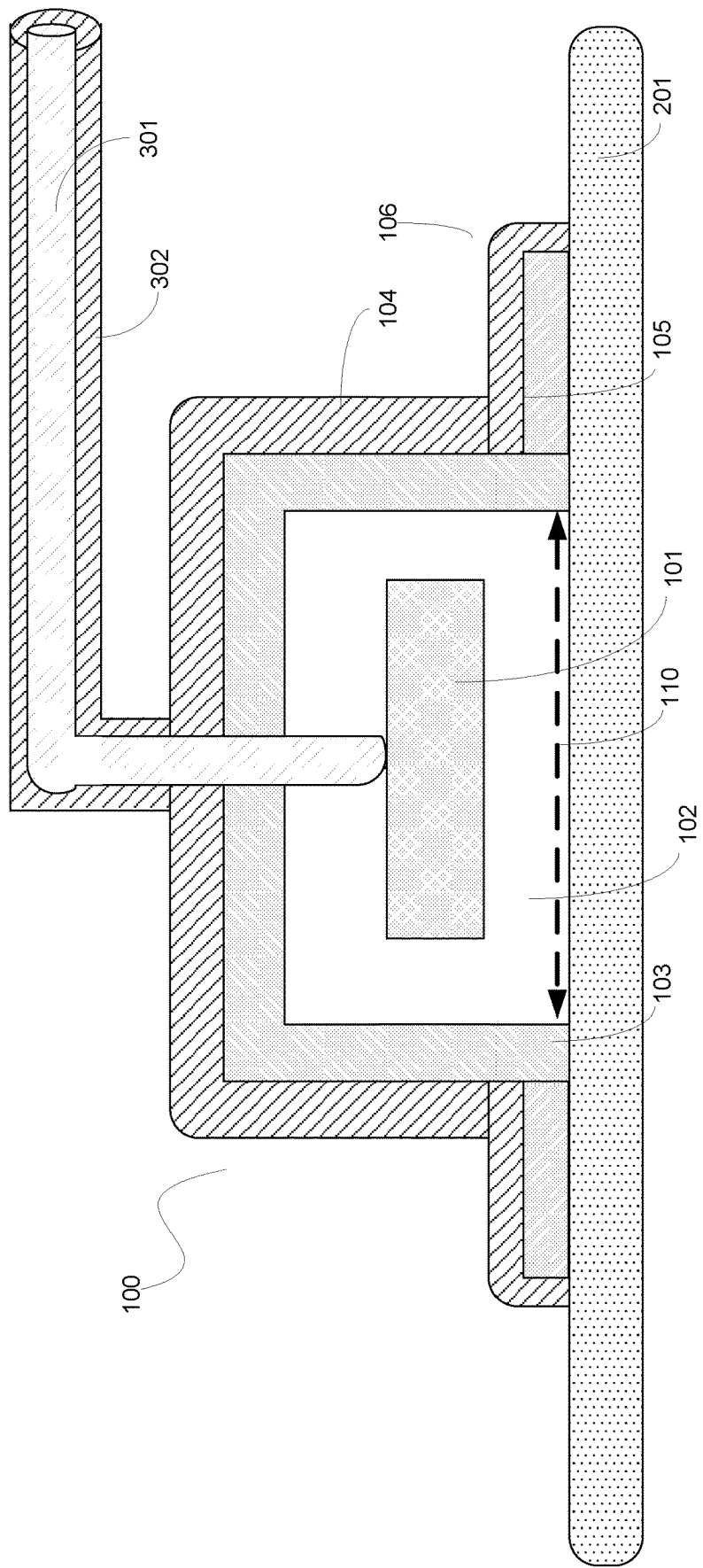
FIG. 3A is a schematic sectional illustration of an EM probe for monitoring at least one biological tissue having a circumferential flange, according to some embodiments of the present invention.
Figure 3B:
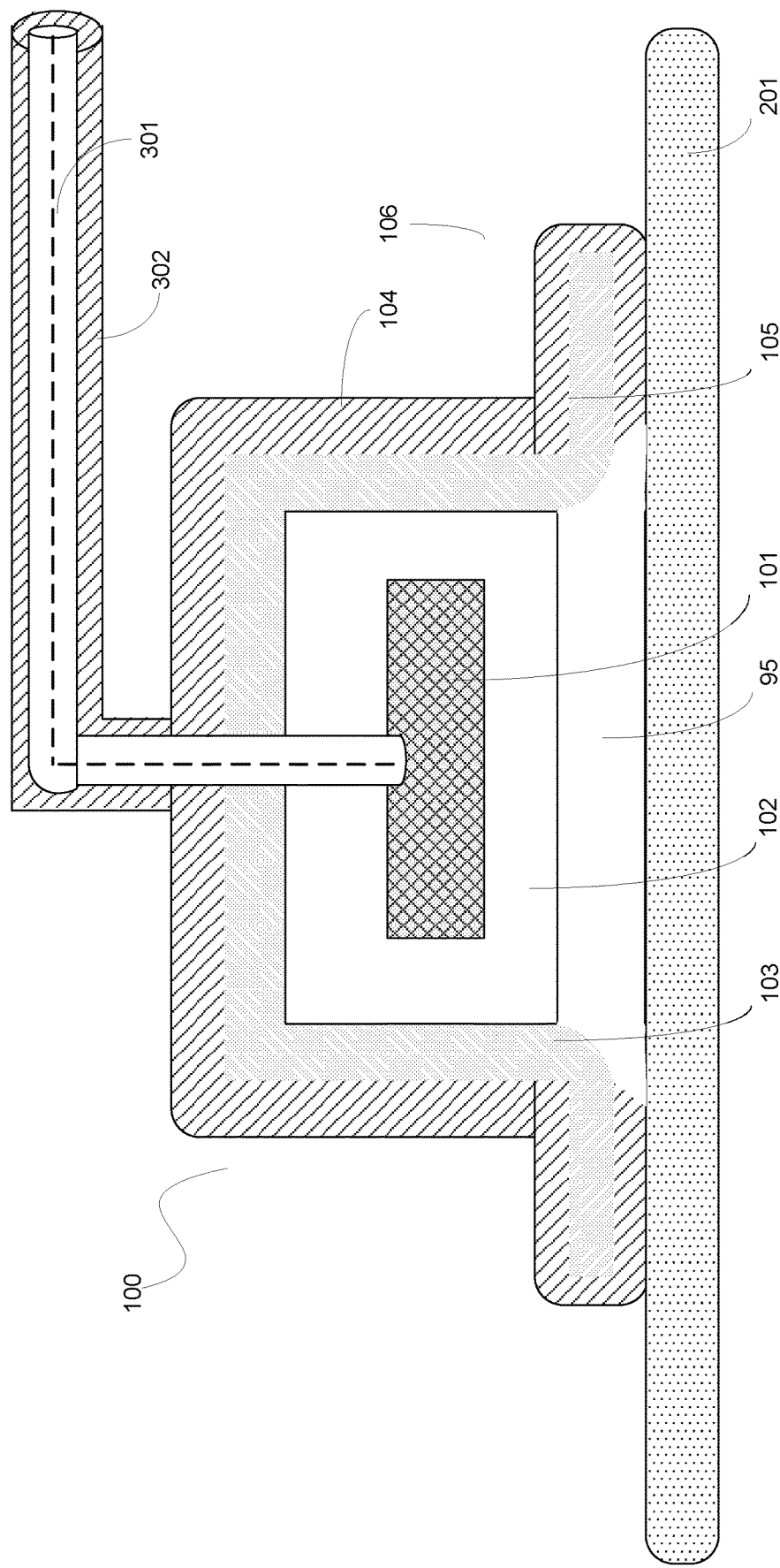
FIG. 3B is a schematic sectional illustration of an EM probe for monitoring at least one biological tissue having a circumferential flange, according to some embodiments of the present invention.

Optionally, the circumferential flange 105 is placed so that in use, the lower part thereof is in touch with or in a close proximity to the skin area 201, for example as shown at FIG. 3, or for instance via a cloth (.i.e. a shirt, pants). Optionally, at least a portion of the circumferential flange 105 is covered by one or more layers of absorbing materials 106 which are in touch with or in a close proximity to the skin area 201. Generally and especially in the case where the EM probe is on top of a cloth, a construction similar to FIG. 3B can be used (at least the area marked with 95 is filled with air only). In this case, pressure is applied to the EM probe 100, for example by use of a chest strap, pushing it towards the body. The pressure applied on the depicted construction concentrates on the circumferential flange 105 and serves to improve mechanical coupling of the circumferential flange 105 to the skin area or, in the case of clothing reduce the gap, created by the layer of clothing.

Optionally, the portion is the edge of the circumferential flange 105, namely the area which is extended away from the cup shaped cavity 103. Optionally, the circumferential flange 105 is placed so that in use, the lower part of the one or more layers of absorbing materials 106 is in touch with or in a close proximity to the skin area 201. In the embodiment depicted in FIG. 2, the inner wire of the connected cable 301 is used for carrying signals intended to and/or received from the emitting and/or receiving elements 101, for brevity referred to herein as an EM element 101. Optionally, the EM element 101 is driven by a coaxial cable 301 whose inner wire and shield are connected to the EM element 101. Optionally, only the inner conductor is connected to the EM element 101. Optionally, the shield is connected and/or coupled to the cup shaped cavity 103.

The circumferential flange 105 conducts EM radiation originating from the cup shaped cavity 103 and/or from the interior volume 102 and/or from the skin area 201, facilitating its absorption in the layers of absorbing materials 106. Optionally, the circumferential flange 105 is continuous and annular. Optionally, the circumferential flange 105 comprises a plurality of separate elements which form a non continuous and annular structure around the opening 110. Optionally, the circumferential flange 105 is continuous and planar.

The circumferential flange 105 increases isolation of the interior volume 102 from interference signals from areas and/or layers that are in the periphery of the EM probe and are superficial, for example the skin layer or fat layer, rather than from internal body tissues and/or organs that are of interest and are substantially in a region that is in front of the opening 110. The circumferential flange 105 effectually guides interference signals, such as close proximity parasitic EM radiation and/or currents traveling on the skin area 201, along the absorbing material 106 so as to dissipate them. In such a manner interfering effects may be reduced or eliminated. The interference signals are the radiation and/or currents which may be from the EM element 101, or from an area external to the EM probe, and travel along the body surface, for example on the skin 201 and/or via proximate subdermal tissues, such as fat and/or organs in close proximity to circumferential flange 105. The isolation of the interior volume 102 from interference signals may reduce the noise caused by parasitic signals originated from the EM transmission of the EM element 101 and/or from external interference signals which are not intercepted from the body of the monitored user. The isolation of the interior volume 102 also reduces the sensitivity to environment changes, such as hand movements or skin changes in proximity to the EM probe 100. In such a manner, for example, the effects of reflection signals originating from hand or other movements in the proximity of the EM probe and/or skin contour changes may be reduced.

Optionally, the distance between the peripheral outer edge of the circumferential flange 105 and the peripheral inner edge thereof is between 0.1 centimeters (cm) and 5 cm and/or a few wavelengths, for example 0.3 cm. Optionally, the circumferential flange 105 is placed, at least partly, inside the interior volume 102.

Figure 4:
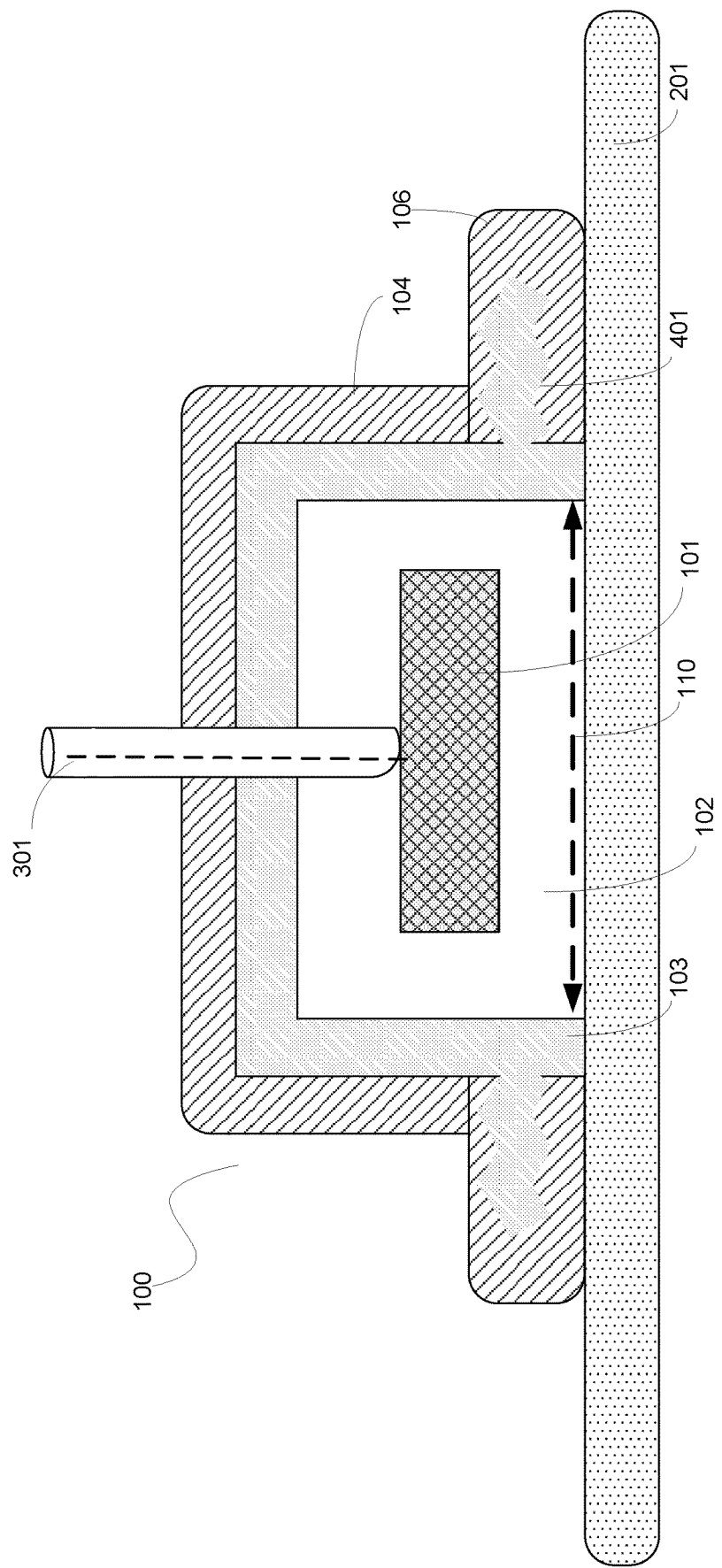
FIG. 4 is a schematic sectional illustration of an EM probe for monitoring at least one biological tissue having a zigzagged circumferential flange, according to some embodiments of the present invention.

Optionally, the circumferential flange 105 is substantially rigid. The larger the surface area of the circumferential flange 105, the higher is the isolation from interference signals. Since the isolation functionality of the circumferential flange 105 and the one or more layers of absorbing materials 106 are more effective when attached to the skin, optionally, at least some of the circumferential flange 105 and the absorbing material 106 which covers it are flexible so as to increase the surface area which is attached to the skin. Optionally, the circumferential flange 105 is substantially flexible, for example made of fiber based structures, flexible polymers, and/or a mesh having shape memory characteristics. This circumferential flange 105 may be bended in order to curve according to the surface of the skin area 201. Optionally, part of the circumferential flange 105 is rigid and part of flange 105 is flexible. In this case the flexible and rigid parts may be coupled or galvanically connected, and each part is coated with the absorbing material 106 separately or jointly. Optionally, the rigid portion is closer to the EM element 101 than the flexible portion, so the nearest volume to the EM element 101 is fixated and possibly pressed against the skin to decrease possible geometrical changes, for example of the skin and fat in proximity to the EM element. Optionally, the circumferential flange is jagged, zigzagged, curved, and/or bended along a plane parallel to the opening 110, for example shown in numeral 401 of FIG. 4. In such a manner, the path signals are passing along the circumferential flange 105 is longer so that their absorption is increased.

Some elements of the EM probe 100 are attached to the body of the monitored user, for example using adhesives, while others are disconnected therefrom.

According to some embodiments of the present invention, the circumferential flange 105 is set to enable an airtight interface between the EM probe 100 and the skin area, enabling attachment by air pressure differences. For example, a sub millimeter layer of silicon material is placed to cover the bottom side of the circumferential flange 105 and to form the airtight interface when attached to a skin area. The airtight interface may also increase the effectiveness of the isolation functionality of the circumferential flange 105 by improving the mechanical coupling of the circumferential flange 105 to the skin area. Optionally, a pressure regulator is attached to the cup shaped cavity 103 so as to control the air pressure in the inner volume of the cup shaped cavity 103. In such a manner, the air pressure differences may be controlled by the user and/or a clinician attaching the EM probe 100. In such an embodiment, the EM probe 100 is constructed to form an air gap above the opening 110. By reducing the air pressure in the gap, the attachment of the EM probe 100 to the skin area is formed. For example the gap created between the horizontal plane of the opening 110 and a plane thereabove in the cup shaped cavity 103. The lower pressure can be created by the pressure regulator, for example one or more one way valves connected to one or more pumps such as rubber balls. Another option is a mechanical lever that deforms the cup shaped cavity 103 after the attachment thereof to the skin area, substantially pulling back the dielectric material away from the skin creating a low pressure air gap.

According to some embodiments of the present invention, the circumferential flange 105 is a detachable element, set to be attached to a skin area above the monitored intrabody volume of the patient. In such an embodiment, the circumferential flange 105 may remain attached to the skin for durations of time in between different monitoring and/or diagnosis sessions, assisting in placement of the EM probe in following sessions. In addition, the ability to detach the cup shaped cavity 103 and optionally the EM element 101 which is mounted therein, allows, for example, cleaning the skin area between the sessions, replacing the cup shaped cavity 103 and/or the EM element 101 and/or repairing elements of the EM probe 100 without having to reposition or attach the circumferential flange 105.

Reference is now made to the isolation of the cable 301. In use, the edge of cable 301, which connects to the EM element 101, is typically close to the skin, parasitic EM radiation radiating from the skin area 201 and/or escaping from the cup shaped cavity 103 and/or originating from other sources may induce parasitic currents on the cable 301 that introduce noise. Optionally, a layer of an absorbing material 302, such as the aforementioned absorbing material, coats the cable 301 in proximity to the external surface of the cup shaped cavity 103. Optionally, the coating is along a portion of the cable 301, starting from the area in close proximity to the cup shaped cavity 103. This coating prevents from parasitic EM radiations which travel along the skin area 201 or passing through the air in proximity to the EM probe 100 from substantially affecting currents conducted by the cable 301 and/or substantially interfering with reception of the signals. This coating also prevents currents conducted on the cable from substantially radiating back into the same or other EM probes and/or their cables. This leakage might interfere with the operation of receiving signals from the monitored area in the body.

In some cases, a network of EM probes, each as shown at 100, is used for receiving and/or capturing signals from the monitored area in the body. In such an embodiment, the sensitivity of this network is greatly determined by the effect of crosstalk interference between the EM probes. Such crosstalk interference includes a reception of an EM signal that is transmitted from the network EM probes and does not propagate through an intended path. This EM signal might propagate on the skin, through air, or through cables or electronics connecting the EM probes, rather than through internal body tissues and/or organs. The crosstalk interference might interfere with the operation of the network and may also increase sensitivity to artifacts that are a result of body movements and changes in the surrounding. The aforementioned isolation isolates the EM probes from one another. Cables connecting the different EM probes might carry some of the signals on their outer shield and therefore should also be protected by the absorbing material as described herein. Moreover, the cables may operate as antennas transferring radiation and inducing currents on proximate cables. Currents induced on the cable of a receiving EM probe by radiation from a cable of a transmitting EM probe may penetrate into the internal volume of the receiving EM probe and therefore introduce noise. The crosstalk signal may be affected by movement of the cable or any respective movements between the cables increasing the overall noise in the system.

Figure 5:
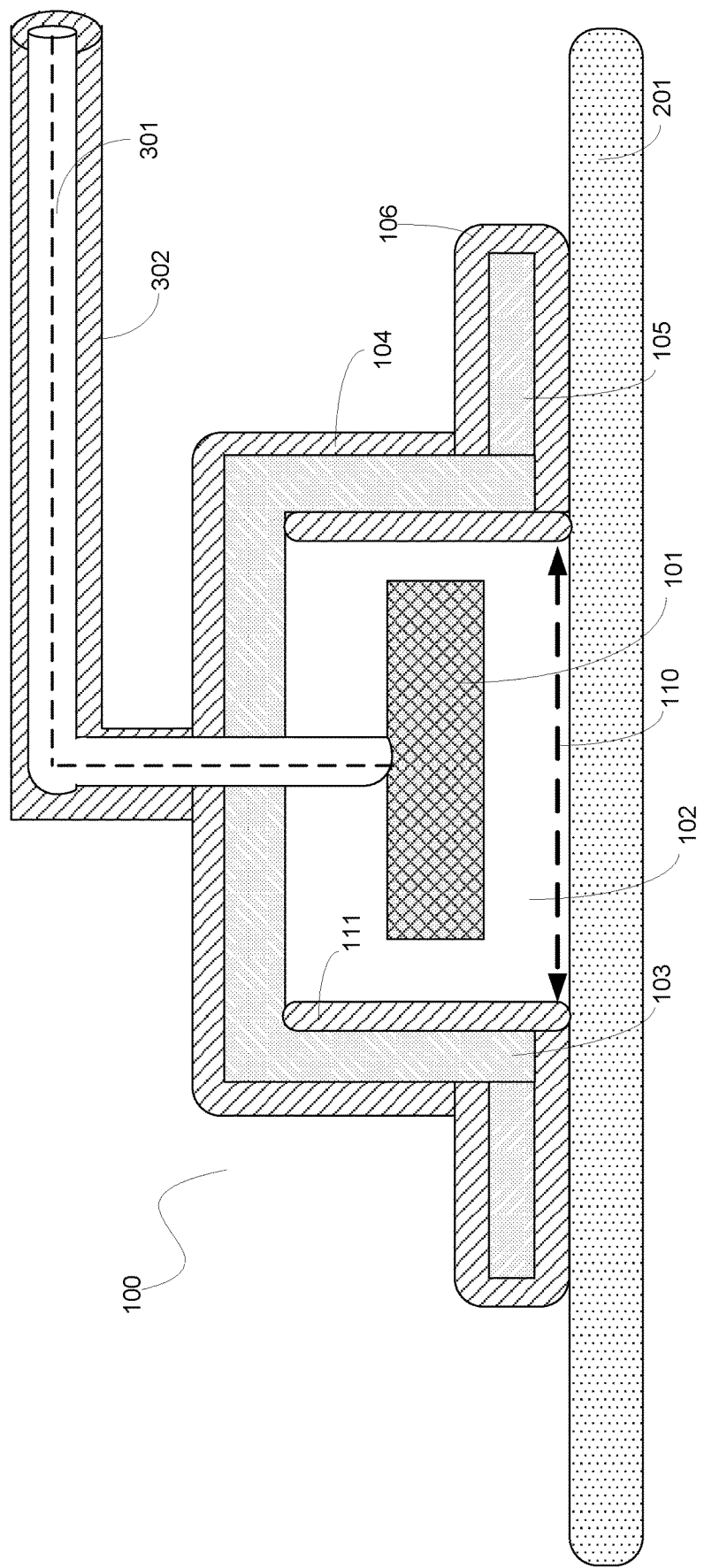
FIG. 5 is a schematic sectional illustration of an EM probe for monitoring at least one biological tissue having a cup shaped cavity with inner walls covered by one or more layers of absorbing materials, according to some embodiments of the present invention.

According to some embodiments of the present invention, some of the inner walls of the cup shaped cavity 103 are covered by one or more layers of absorbing materials, such as the aforementioned absorbing materials, for example as depicted by numeral 111 in FIG. 5. Optionally, the lateral walls of the cup shaped cavity 103 are covered with the aforementioned absorbing materials. Optionally, the lateral walls of the cup shaped cavity 103 and the circumferential flange 105 are covered with the aforementioned absorbing materials so that none of them touches the skin of the patient.

Optionally, all the inner walls of the cup shaped cavity 103 are covered with the aforementioned absorbing materials. Optionally only the portions of the inner walls which are closer to the opening 110 are covered with the layers of absorbing materials 111. For example, FIG. 6 depicts a cup shaped cavity which is shaped as a dome. The circumferential flange 105 is encircled and marked with numeral 105.

Optionally, only the inner wall of the cup shaped cavity 103 which faces the opening 110 remains uncovered by layers of absorbing material, for example as shown at FIG. 5.

It should be noted that layers 104, 106, 111 and 302 employ an absorbing material in proximity to conducting parts such as the cup shaped cavity 103, the circumferential flange 105 and/or the connected cable 301 so that parasitic EM signals and radiation traveling along these parts may be dissipated. In such a manner, interference signals, which propagate in close proximity to the EM element 101, are absorbed in one or more of the layers 104, 106, 111 and 302. The interference signals may be signals originated from the EM element 101, signals entering the interior volume 102 from the skin area 201, and/or straying signals which do not arrive from an intended path, i.e. parasitic signals.

According to some embodiments of the present invention, the EM element 101 is connected, via the cable 301, to a receiver and/or a transmitter which may be located in a different housing, for example in a mobile or a stationary unit, or within an element that is integrated with the EM probe, externally to the cup shaped cavity 103. Optionally one or more attachment elements, as defined below, are used for attaching the EM probe 100 to the monitored user so that the opening 110 faces the skin area 201, for example as shown in FIGS. 1-4.

Reference is now also made to FIGS. 7A and 7B, which are schematic illustrations of an EM probe 150 having an EM element generating EM radiation, which is placed outside of the interior volume of the cup shaped cavity 103, according to some embodiments of the present invention. In such an embodiment, a conducting element, such as a waveguide, is used for conducting EM radiation, such as RF and/or MW waves which are generated outside of the cup shaped cavity 103 and conducted into the interior volume thereof. At least the lower portion of the circumferential flange around the opening is covered with an absorbing material 155, as described above. Optionally, also the external lower part of the cup shaped cavity 103 is covered with the absorbing material 155.

Figure 8:
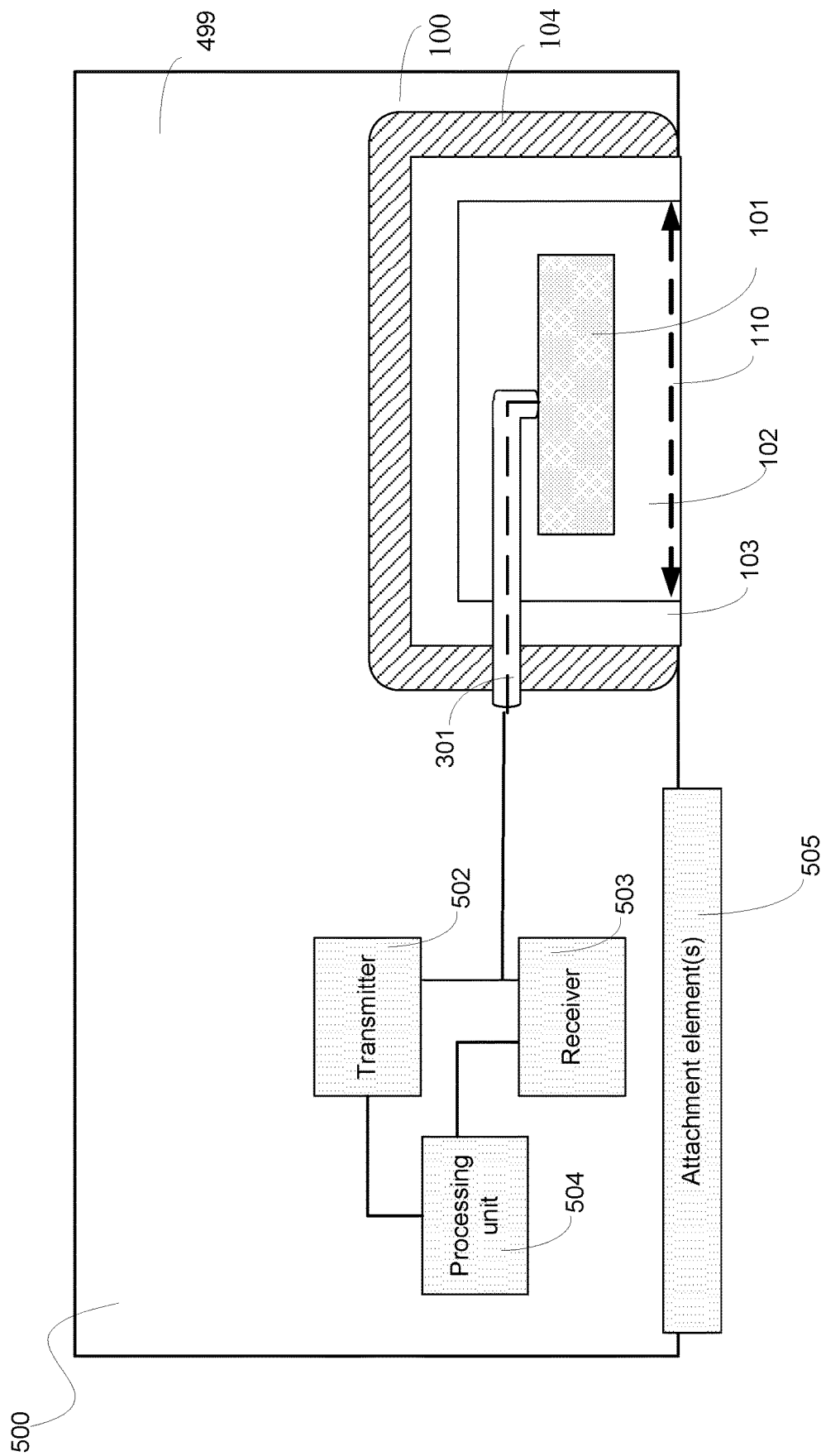
FIG. 8 is a schematic sectional illustration of a wearable device having an EM probe for monitoring at least one biological tissue, according to some embodiments of the present invention.

Reference is now made to FIG. 8, which is a sectional schematic illustration of a wearable device 500 for monitoring a biological tissue(s), according to some embodiments of the present invention. The wearable device 500 include a housing 499 which contains one or more of the EM probe 100 and one or more additional components for monitoring a monitored user, optionally ambulatory, and optionally for detecting one or more physiological patterns according to a dielectric property, for example as described in International patent application pub. No WO 2010/100649, International patent application pub. No WO 2009/031150, and/or International patent application pub. No 2009/031149, which are incorporated herein by reference. The dielectric property is calculated based on the reading of the EM radiation captured by the EM element. Optionally, a transmitter 502 is used to generate a signal that is transmitted to the EM element 101 for transmission. Optionally, a receiver 503 is used to receive a signal that is received by the EM element 101. Optionally, the processing unit 504 is a microprocessor or any other computing unit used to analyze the outputs of the receiver 503 and/or to control the transmitter 502. The processing is optionally performed as described in International patent application pub. No WO 2010/100649, International patent application pub. No WO 2009/031150, and/or International patent application pub. No 2009/031149, which are incorporated herein by reference. Optionally, the wearable device 500 includes one or more attachment elements 505, such as straps, coatings of adhesive. When straps are used, the wearable device 500 may be placed above a cloth (i.e. shirt, pants). Adhesive elements, and buckle components, for attaching the wearable monitoring apparatus 500 to the body of a monitored user with the opening 110 facing a skin area (not shown). In another embodiment of the present invention, such attachment elements 505 may be used for connecting only the EM probe 100 to the skin area. It should be noted that the components described in FIG. 8 may be part of a stationary system in which only the EM probe 100 is attached to the body of the monitored user.

Figure 9:
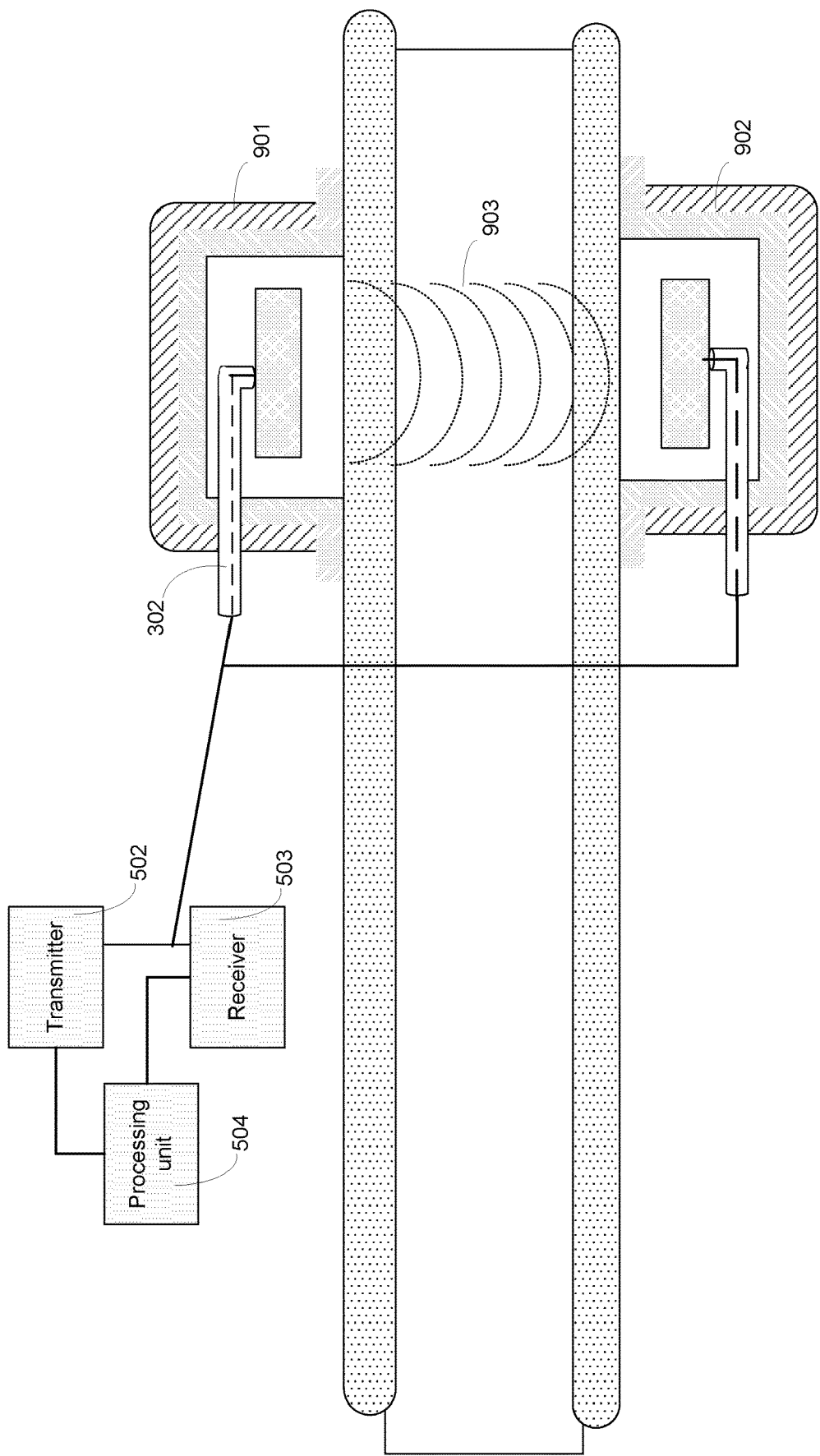
FIG. 9 is a sectional schematic illustration of a system for monitoring a biological tissue(s) by an analysis of passing through signals, according to some embodiments of the present invention.

Reference is now made to FIG. 9, which is a sectional schematic illustration of a system 500 for monitoring a biological tissue(s) by an analysis of passing through signals 903, according to some embodiments of the present invention. Components 502-504 are as depicted in FIG. 8, however in these embodiments at least two EM probes 901, 902 are used. One EM probe 901 is used for transmitting EM radiation toward a body organ or a number of body tissues and another EM probe 902 is used for receiving the passing through EM radiation 903. Optionally, the transmitting EM probe 901 is also set to receive reflections of the EM radiation from the body part. Optionally, the EM probe 902 is also set to transmit EM radiation toward the body part. Each one of the EM radiation EM probes 901, 902 may be defined as any of the aforementioned embodiments. In such an embodiment the intended path can be, for example, the path passing from EM probe 902 to EM probe 901. The isolation properties as described in the aforementioned may serve to minimize interference to the reception of EM radiation from this path.

Figure 10A:
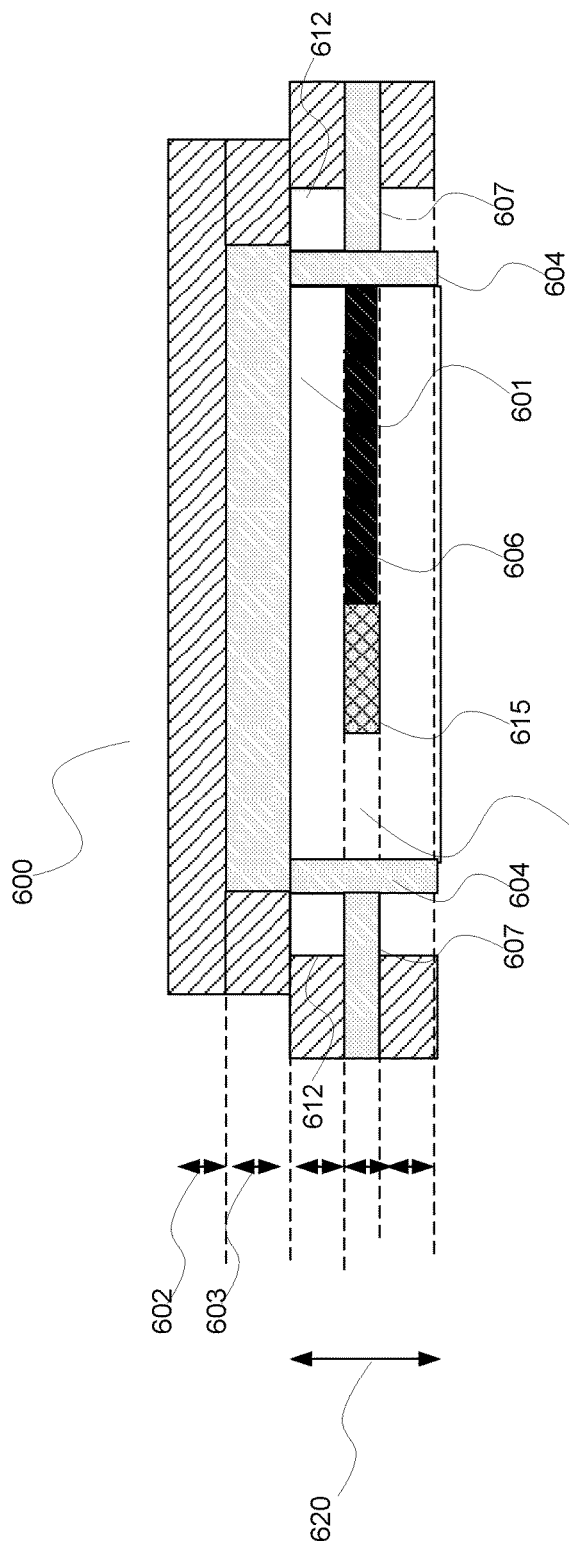
FIG. 10A and FIG. 10B which are a sectional schematic illustration and a three dimensional illustration of a printed circuit board (PCB) EM probe having a fabricated cup shaped cavity, according to some embodiments of the present invention.
Figure 10B:
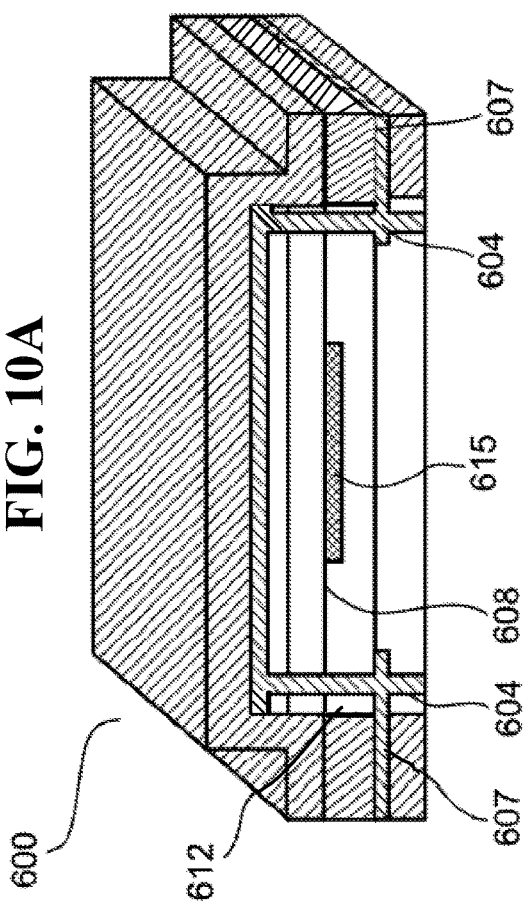

Reference is now made to FIG. 10A, which is a sectional schematic illustration of a printed circuit board (PCB) EM probe 600 having a fabricated cup shaped cavity 601 and to FIG. 10B which is a three dimensional schematic illustration of this PCB EM probe 600, according to some embodiments of the present invention. The PCB EM probe 600 is created by a number of layers. As shown at 602, a layer of absorbent material, such as Eccosorb® MCS, is placed above a layer of conductive material 603, such as a metal layer. A stratified layer 620 below the conductive material 603 is constructed. The stratified layer 620 includes lateral walls 604, which are formed around a dielectric substance 608 having a relatively high dielectric coefficient, for example about 10, such as Rogers R3010, for example as described above. A conducting element 606, such as a wire, is placed in the dielectric substance 608, optionally in parallel to the layer of conductive material 603, and is extended outside the PCB EM probe through the lateral walls with no electrical connection to them. Another electrical connection (not shown) is possibly made and extended to the outside of the PCB EM probe, in a similar manner to the EM element 615 or to the fabricated cup shaped cavity. This allows connecting an EM element 615, such as an antenna thereto. In such a manner, an internal volume is formed contained within the reflecting walls 604 and the layer of conductive material 603.

According to some embodiment of the present invention the PCB EM probe 600 may be created by fabricating and bonding 4 layers, using fabrication techniques. For example, each layer is fabricated from a "blank PCB" made of a bonded metal, for example copper, and a substrate such as Rogers R3010. The metal on the "blank PCBs" are etched away and the layers are then bonded together. The layers in such an embodiment can be comprised of the following layers:

1) a first layer the top of the formed cup shaped cavity and underneath it a substrate,
2) a second layer an additional substrate and underneath an etched antenna and one or more conducting wires feeding it,
3) a third layer—an additional substrate and underneath it an etched peripheral circumferential flange, and
4) a fourth layer—a bare substrate layer with no metal.

These 4 layers are bonded together where the first layer is the topmost layer and fourth layer is the bottom layer. Optionally, the lateral wall(s) 604 are made by drilling dense via holes and filling them with a conductive material. Such dense via holes, optionally with metal connecting among them in each horizontal layer, may function as a metal plate for wavelengths greater than the distance between each pair of dense via holes. When such via holes are drilled in said substrate some dielectric material may remain effectively outside the cup shaped cavity due to fabrication limitations, for example 612 as in FIG. 10A. Optionally, the four layers are sized and shaped as in FIG. 10B. Optionally, a shaped absorbing material is bonded on the top of the created PCB EM probe and on the bottom side of the flange. Electronic circuitry like amplifiers, transformers, filters, receivers and transmitters, data collector and/or communication modules may be constructed between each pair of layers. For example, additional layers can be added on top of the cup and use the conductive upper part of the cap as a ground plane. This electronic circuitry can then be put inside an additional cavity. Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Figure 11A:
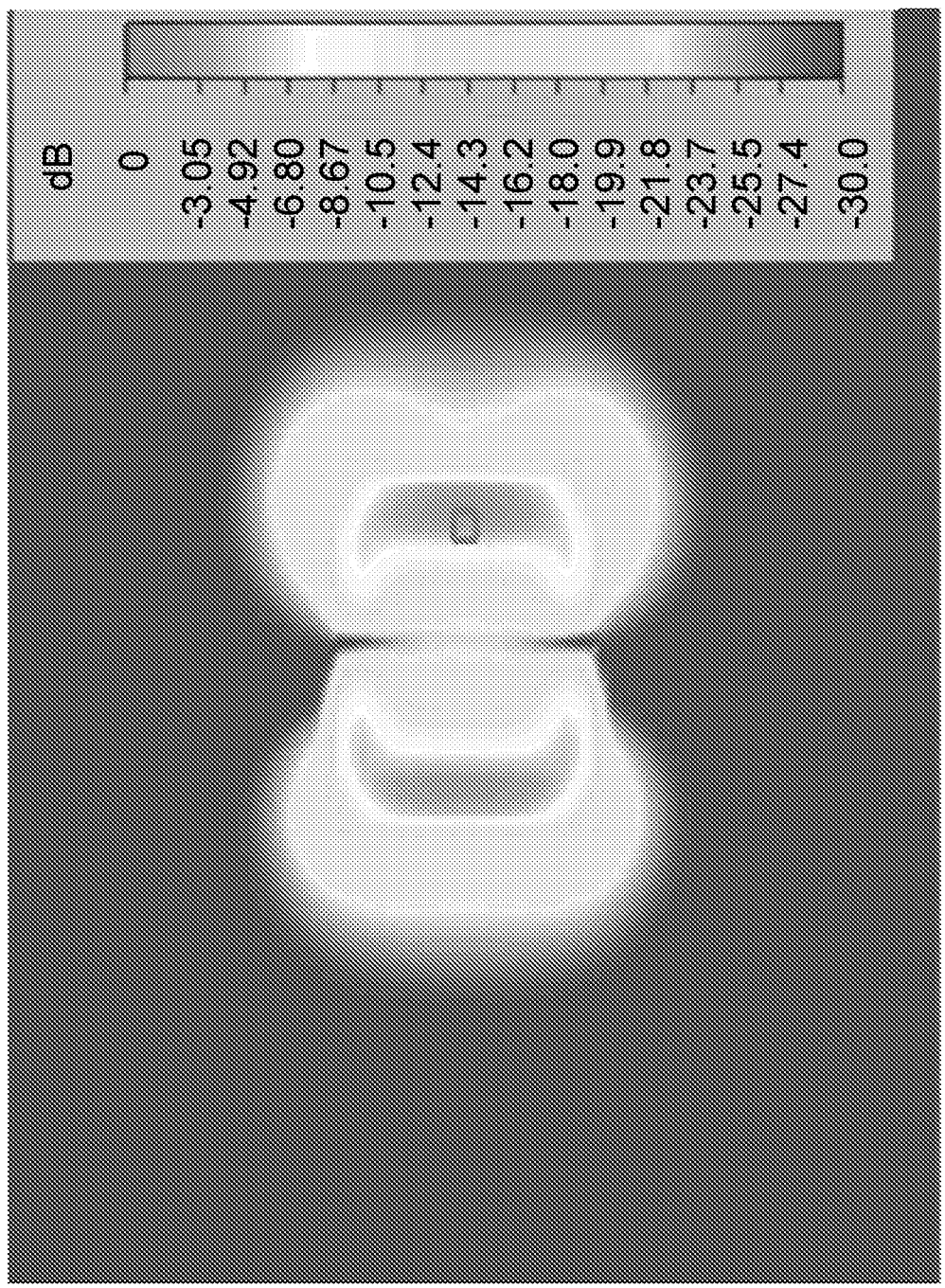
FIGS. 11A, 11B and 11C are images of surface current density in an EM probe without a layer of absorbing material, in an EM probe with a layer of absorbing material, and in an EM probe with a layer of absorbing material covering the bottom side only of a circumferential flange, according to some embodiments of the present invention.
Figure 11B:
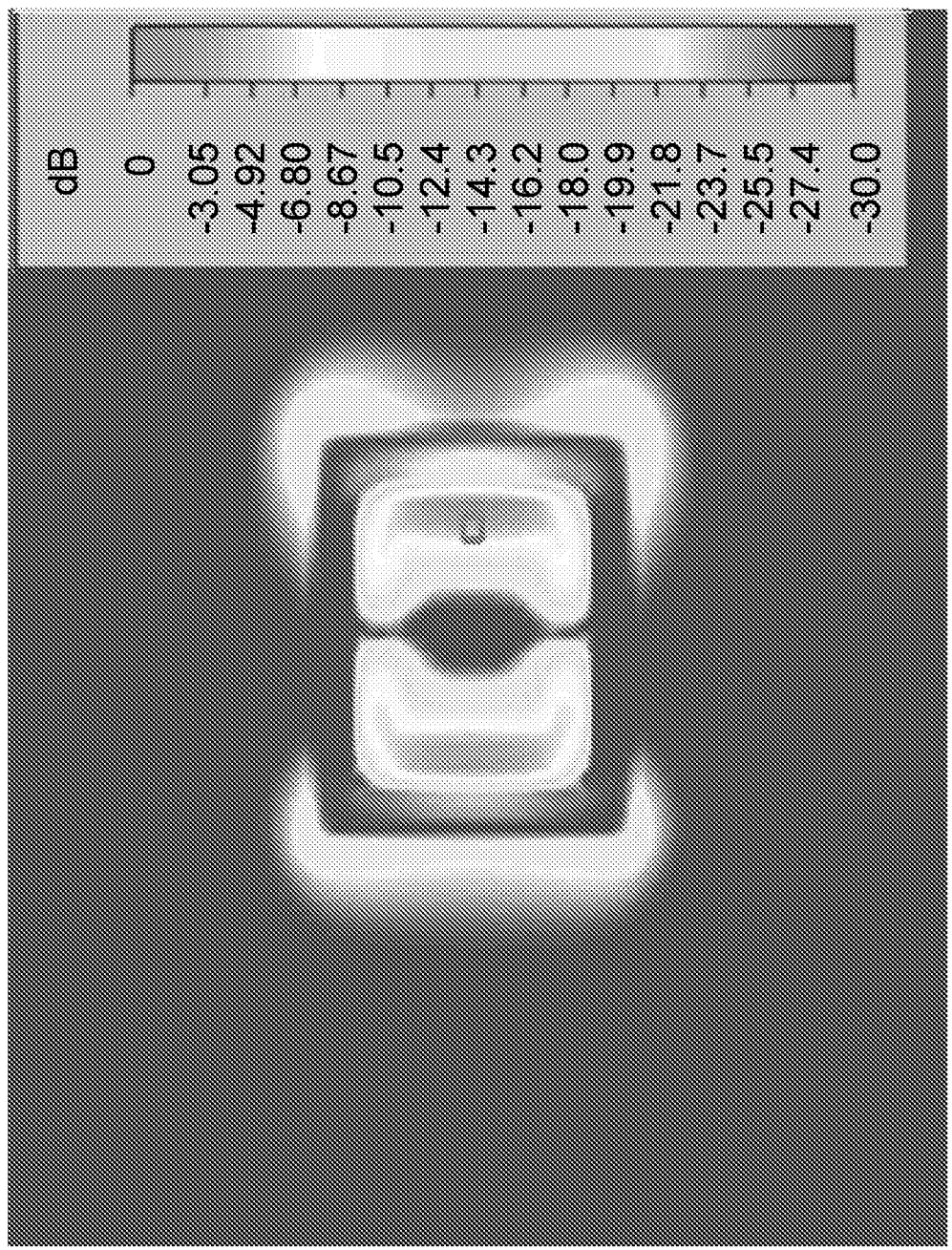
Figure 11C:
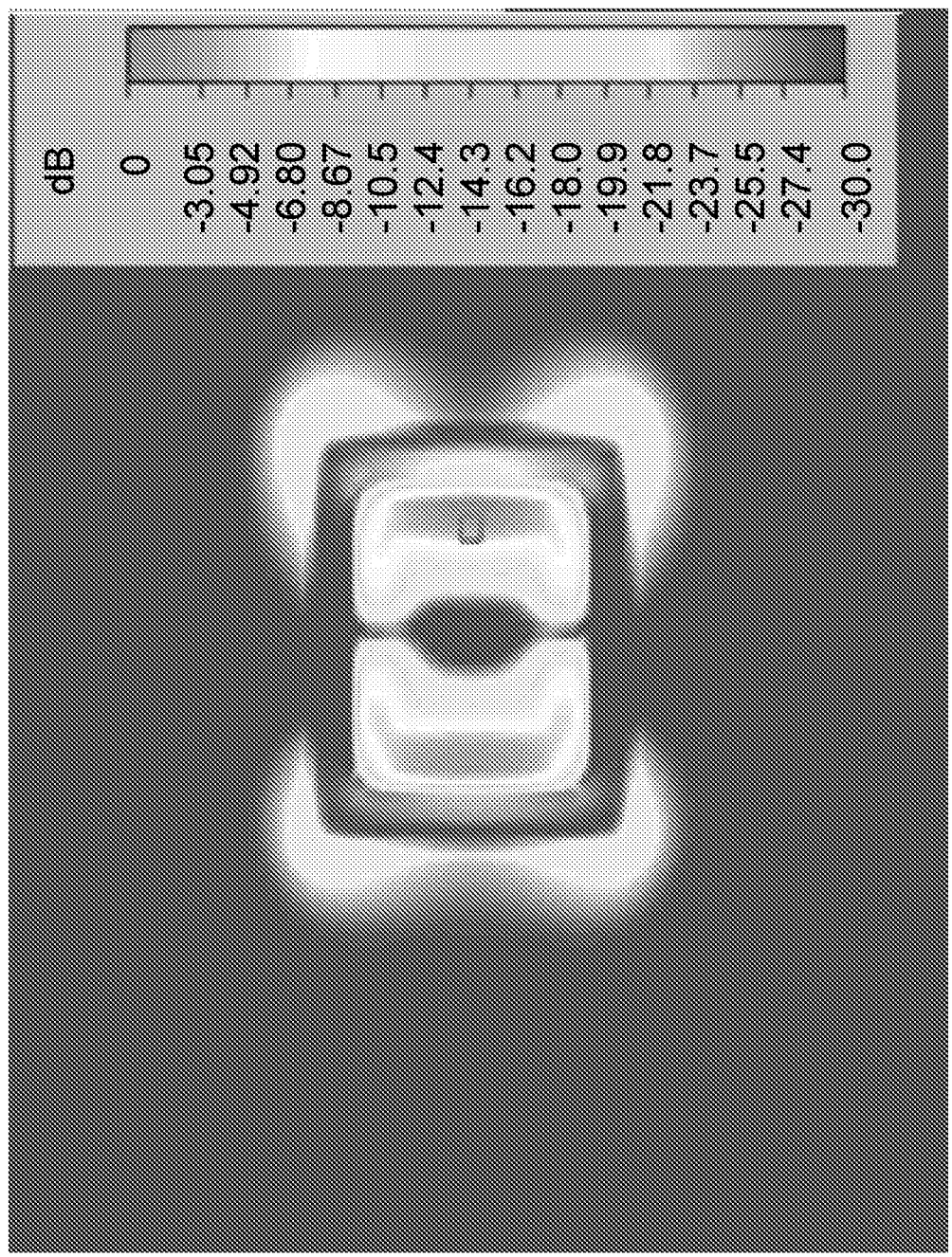
Figure 12A:
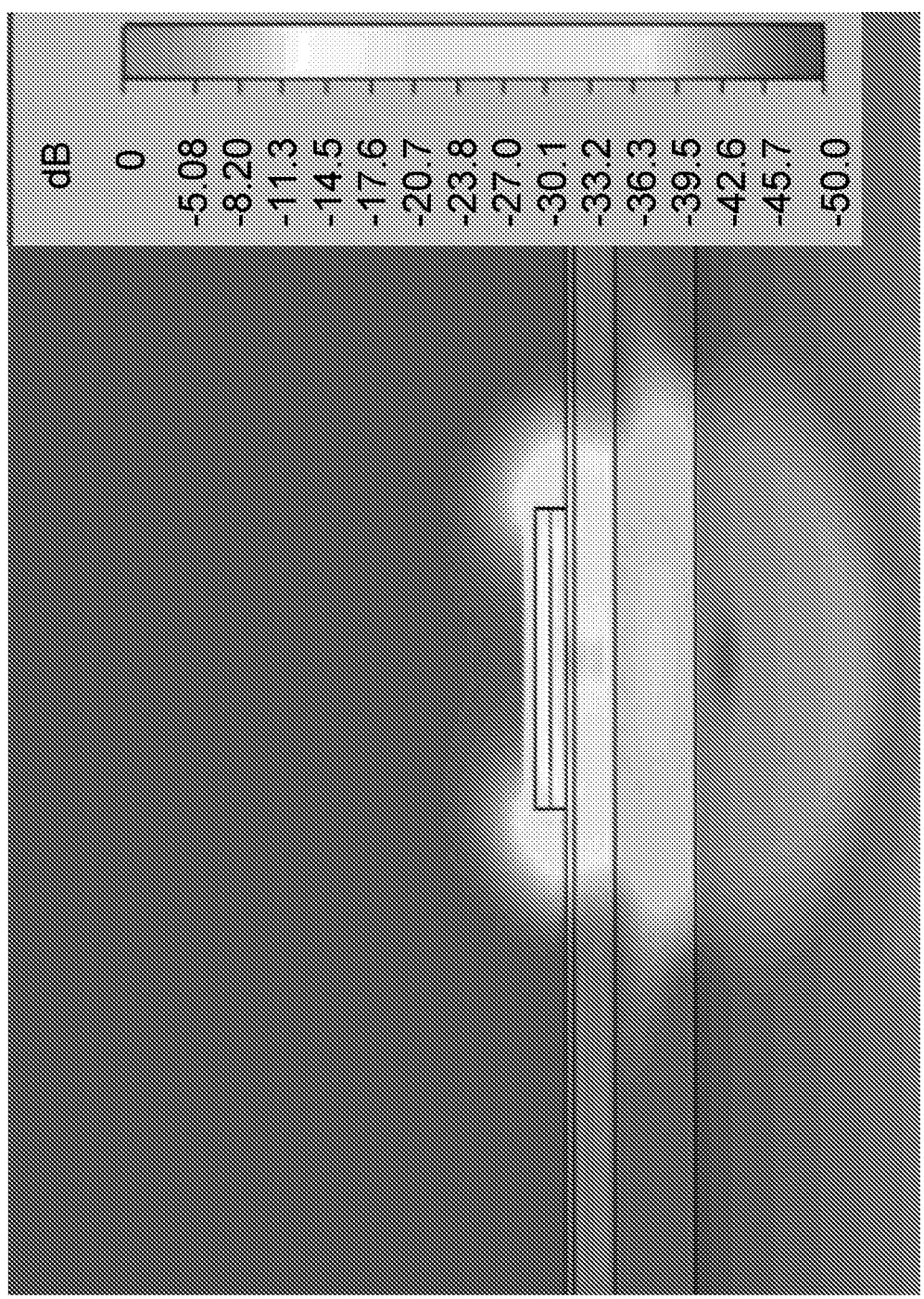
FIGS. 12A and 12B and 12C are images of H-field distribution in an EM probe without a layer of absorbing material, in an EM probe with a layer of absorbing material, and in an EM probe with a layer of absorbing material covering the bottom side only of a circumferential flange, according to some embodiments of the present invention.
Figure 12B:
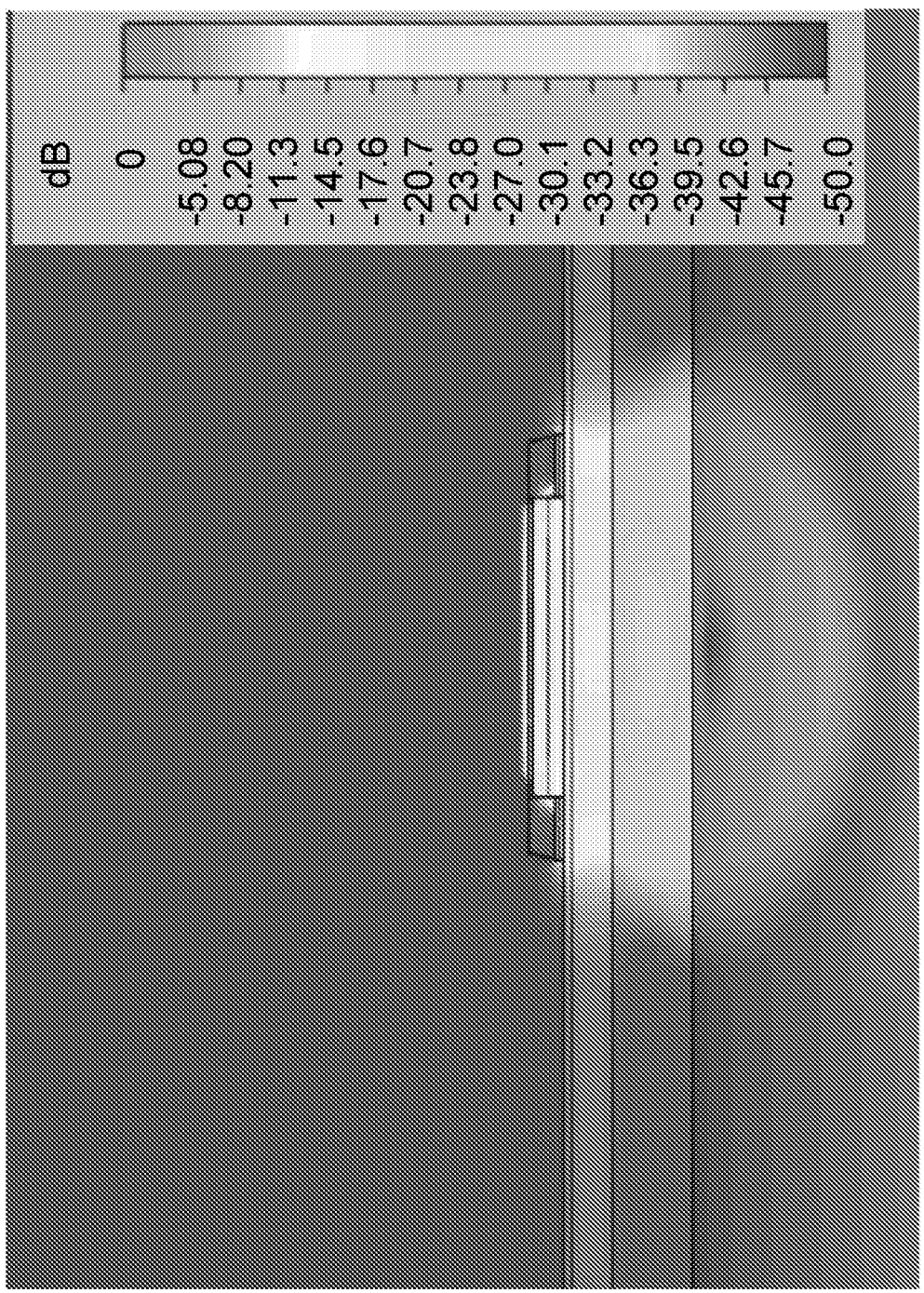
Figure 12C:
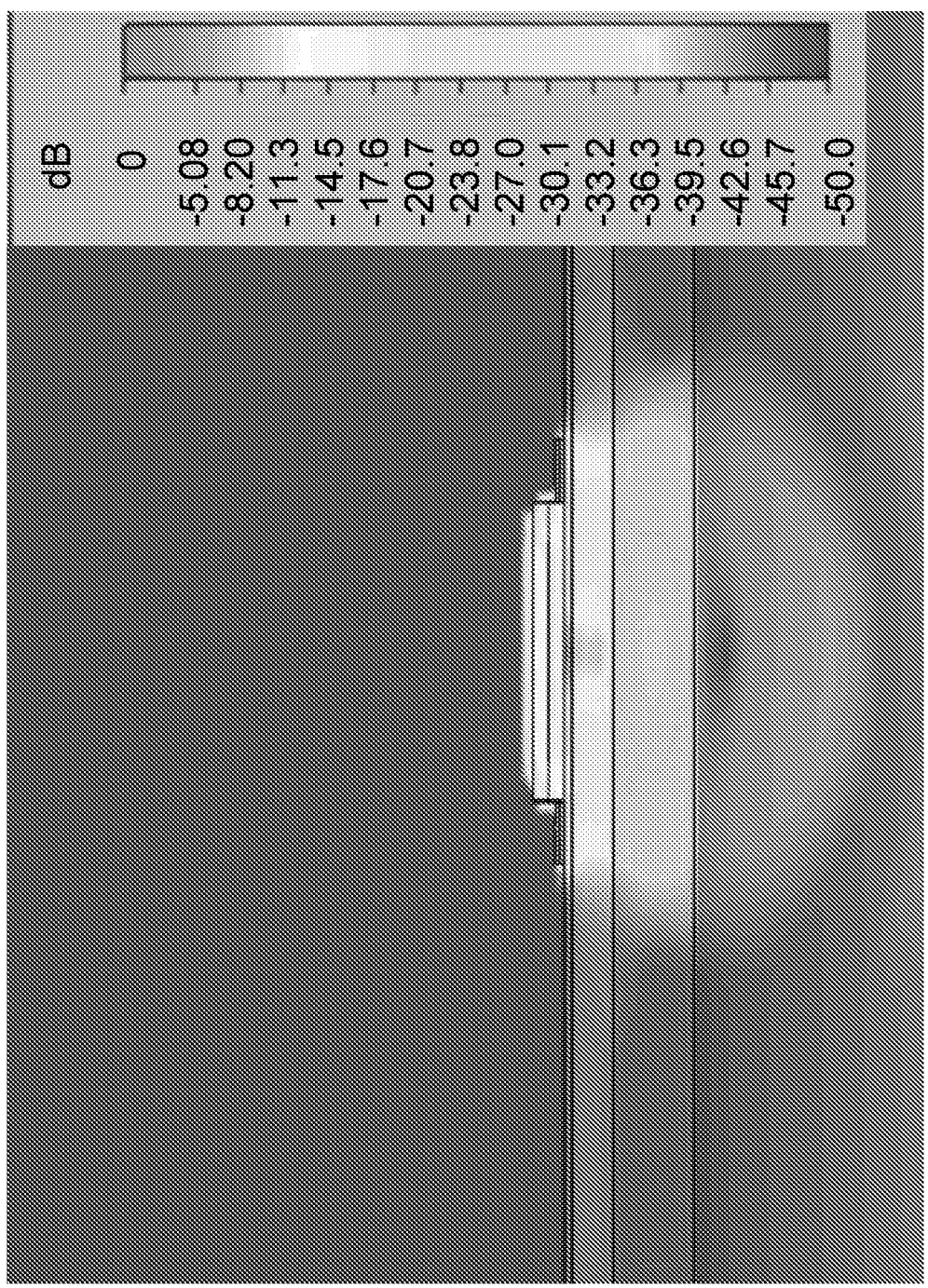
Figure 13A:
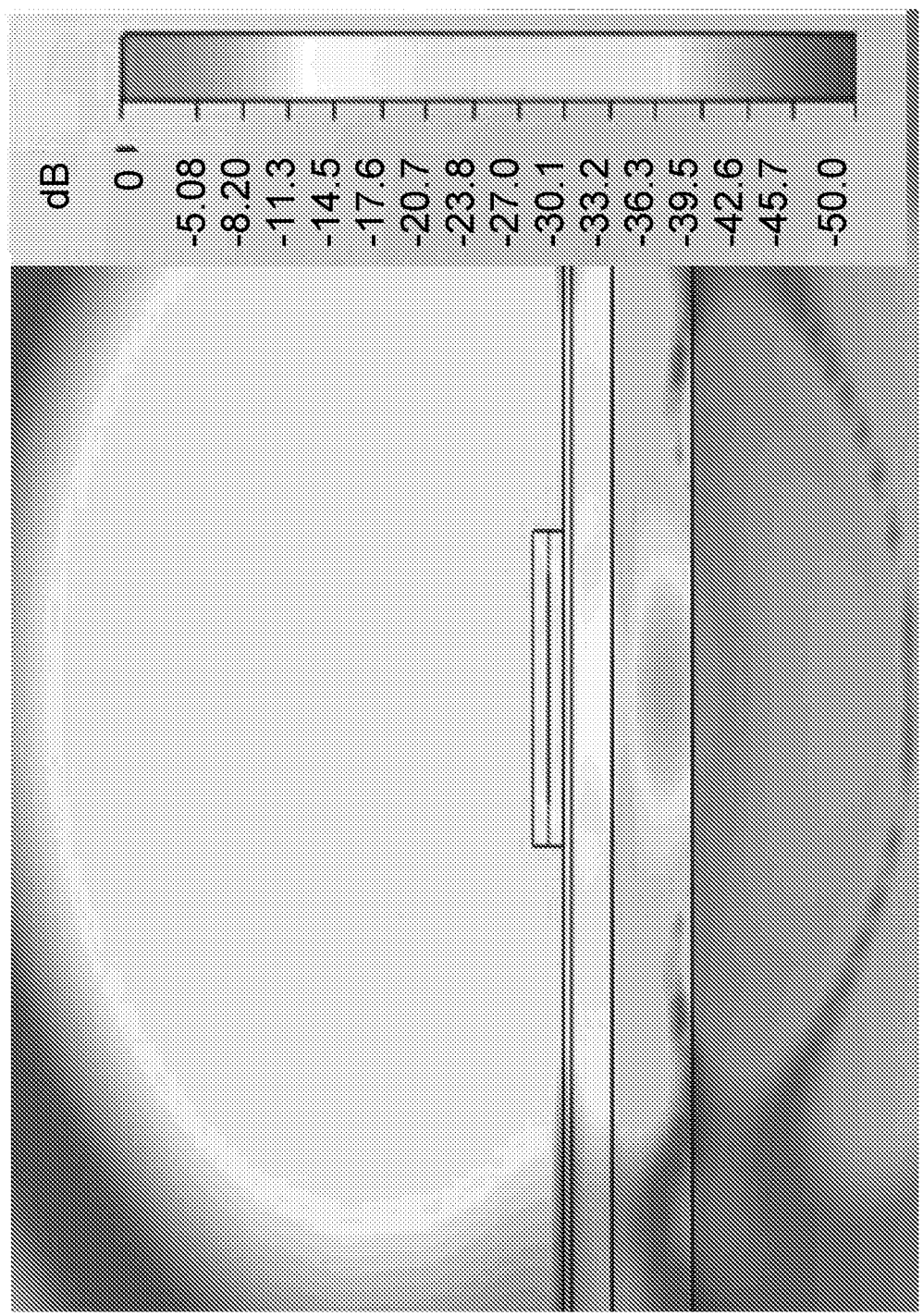
FIGS. 13A and 13B and 13C are images of E-field distribution in an EM probe without a layer of absorbing material, in an EM probe with a layer of absorbing material, and in an EM probe with a layer of absorbing material covering the bottom side only of a circumferential flange, according to some embodiments of the present invention.
Figure 13B:
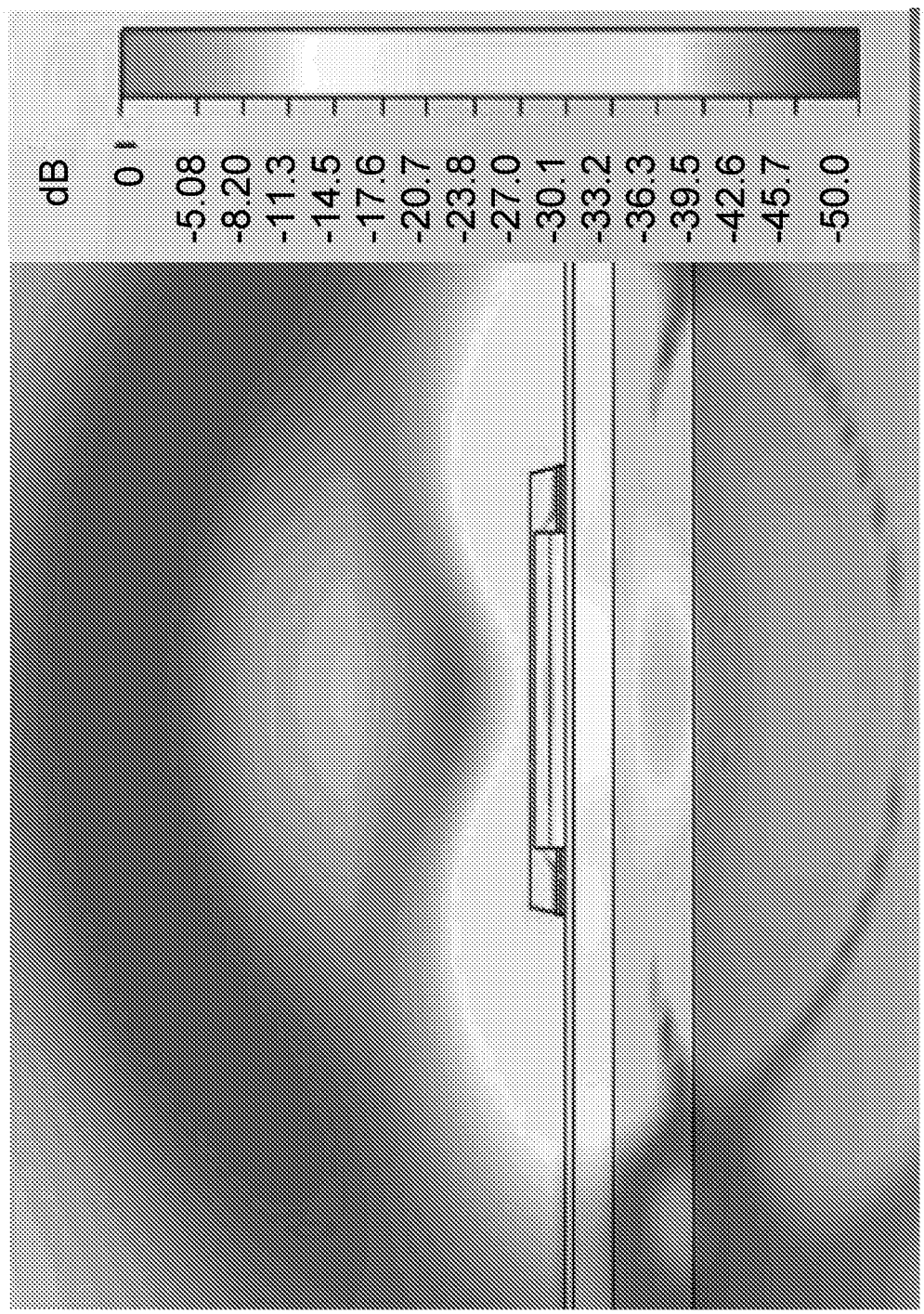
Figure 13C:
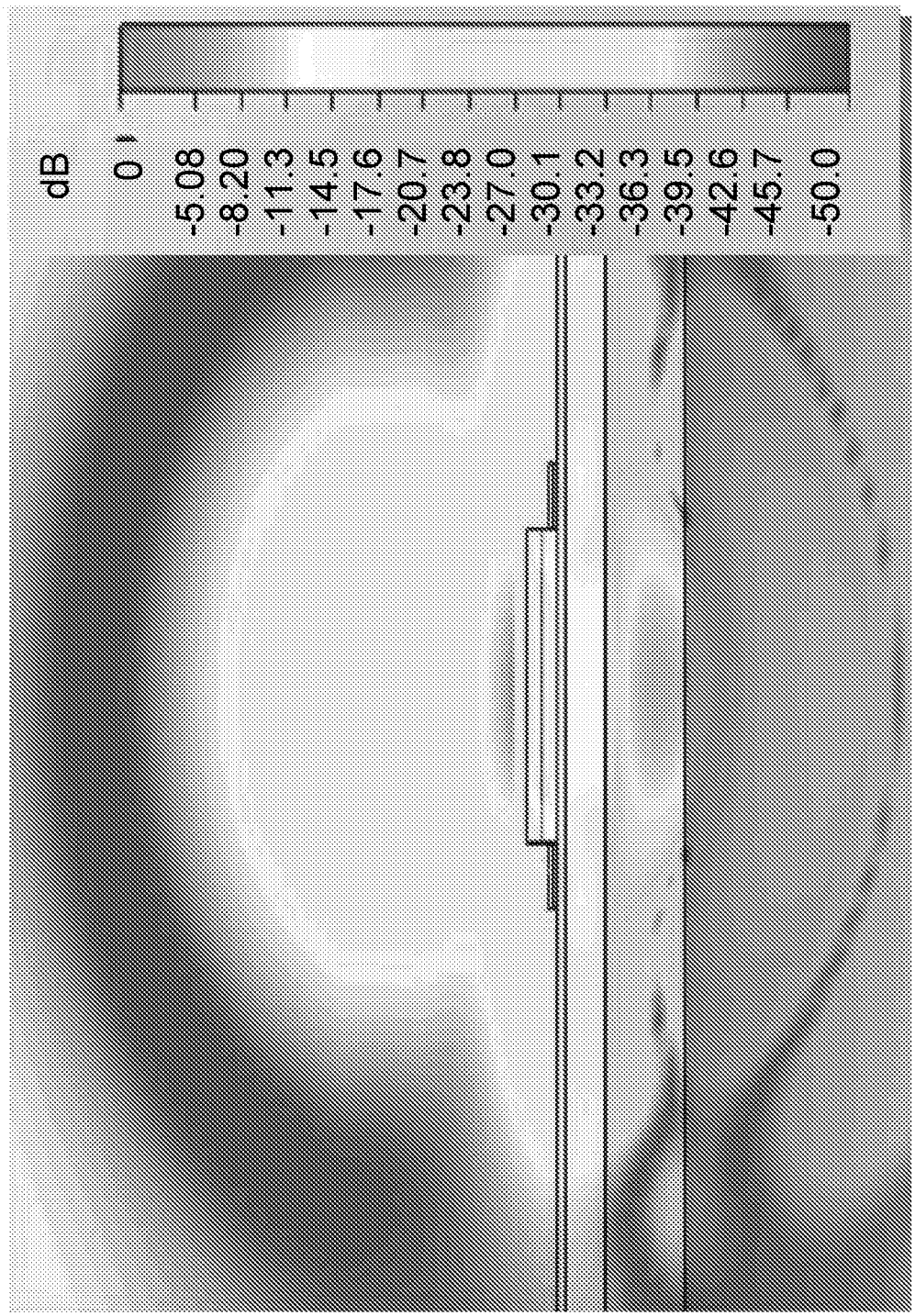

Reference is now made to FIGS. 11A, 11B and 11C, which are images of respectively, surface current density in an EM probe without a layer of absorbing material and a surface current density in an EM probe with a layer of absorbing material covering both sides of a circumferential flange as well as covering a cup shaped cavity, and a current density in an EM probe with a layer of absorbing material covering the bottom side only of a circumferential flange, according to some embodiments of the present invention. Reference is also made to FIGS. 12A, 12B and 12C, which are images of, respectively, H-field distribution in an EM probe without a layer of absorbing material and a H-field distribution in an EM probe with a layer of absorbing material covering both sides of a circumferential flange as well as covering a cup shaped cavity, and an H-field distribution in an EM probe with a layer of absorbing material covering the bottom side only of a circumferential flange, according to some embodiments of the present invention. Reference is also made to FIGS. 13A, 13B and 13C, which are images of, respectively, E-field distribution in an EM probe without a layer of absorbing material, E-field distribution in an EM probe with a layer of absorbing material covering both sides of a circumferential flange as well as covering a cup shaped cavity, and an E-field distribution in an EM probe with a layer of absorbing material covering the bottom side only of a circumferential flange, according to some embodiments of the present invention. FIGS. 11-13 depict a simulation of an EM probe having an antenna mounted in an inner volume of a cup shape cavity. The antenna radiates RF radiation in a frequency belonging to band of about 0.4 Ghz or 0.9 Ghz or 2.4 Ghz or 5.6 Ghz or belonging to a UWB band, for example in 3-6 Ghz band, or another frequency or band in the UHF band. The sizes of the cup shape cavity is optionally of a square shape of dimension about 2, 4, 5, 7, 10, 13, 17 or 20 centimeters and the antenna is sized to spanning 20, 30, 50, 80, 90, or 95% of the width of the cavity. As depicted by these figures, the layer of absorbing material isolates the radiated area and limits it to the inner volume of the EM probe.

It is expected that during the life of a patent maturing from this application many relevant devices and methods will be developed and the scope of the term transducer, cavity, absorbing material, and controller is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An electromagnetic (EM) probe for monitoring at least one biological tissue, comprising:
   a dome shaped cavity having an opening and an interior volume;
   a circumferential flange formed substantially around the dome shaped cavity, in proximity to the opening;
   at least one layer of a material, for absorbing electromagnetic radiation, covering an inner surface of the circumferential flange; and
   an emitting element configured for at least one of emitting and capturing EM radiation and electrically connected to at least one of an EM receiver and an EM transmitter;
   wherein a location of the material on the lateral walls and the inner surface of the circumferential flange is selected for contacting a skin of a subject in use when the EM probe is applied to the skin, such that the dome shaped cavity and the circumferential flange does not contact the skin of the subject.

2. The EM probe of claim 1, wherein the circumferential flange is an extension of the dome shaped cavity.

3. The EM probe of claim 1, wherein the circumferential flange is curved, following a curvature of the dome shape cavity.

4. The EM probe of claim 1, wherein the circumferential flange has a convex shape and the dome shaped cavity has a concave shape.

5. The EM probe of claim 1, wherein the dome shaped cavity and the circumferential flange are made of a conductive material.

6. The EM probe of claim 1, wherein the material covers lateral walls of the dome shaped cavity and the circumferential flange.

7. The EM probe of claim 1, wherein the opening is formed between the material for absorbing electromagnetic radiation, covering lateral walls of the dome shaped cavity and the circumferential flange.

8. The EM probe of claim 1, wherein an inner wall of the dome shaped cavity facing the opening is uncovered by the material.

9. The EM probe of claim 1, wherein an exterior surface of the dome shaped cavity and the circumferential flange is covered by the material.

10. The EM probe of claim 9, wherein an entire of the exterior surface of the dome shaped cavity and the circumferential flange extending to a rim of the circumferential flange is covered by the material.

11. The EM probe of claim 1, wherein a portion of a rim of the circumferential flange, sandwiched between the material covering the inner surface of the circumferential flange and the material covering an exterior surface of the circumferential flange.

12. The EM probe of claim 1, wherein the at least one layer of the material further covers inner walls of the dome shaped cavity.

13. A method of producing an electromagnetic (EM) probe for monitoring at least one biological tissue, comprising:
providing a dome shaped cavity having an opening and an interior volume, and including a circumferential flange formed substantially around the dome shaped cavity, in proximity to the opening;
applying at least one layer of a material, for absorbing electromagnetic radiation, over an inner surface of the circumferential flange;
placing an emitting element configured for at least one of emitting and capturing EM radiation; and
electrically connecting the emitting element to at least one of an EM receiver and an EM transmitte;
wherein the material on the lateral walls and the inner surface of the circumferential flange is placed for contacting a skin of a subject in use when the EM probe is applied to the skin, such that the dome shaped cavity and the circumferential flange does not contact the skin of the subject.

14. The method of claim 13, wherein the dome shaped cavity is formed from layers of a printed circuit board (PCB).

15. The method of claim 13, wherein the material is applied over lateral walls of the dome shaped cavity and the circumferential flange.

16. The method of claim 13, wherein the material is applied to cover the lateral walls of the dome shaped cavity and the circumferential flange for reducing a diameter of opening dome shaped cavity without the applied material.

17. The method of claim 13, wherein no material is applied to an inner wall of the dome shaped cavity facing the opening.

18. The method of claim 13, further comprising applying the material to an exterior surface of the dome shaped cavity and the circumferential flange.

19. The method of claim 13, wherein an entire of the exterior surface of the dome shaped cavity and the circumferential flange extending to an rim of the circumferential flange is covered by the material.

20. The method of claim 13, further comprising applying the at least one layer of the material over inner walls of the dome shaped cavity.

* * * * *